US006254861B1

(12) United States Patent
Choudhury

(10) Patent No.: US 6,254,861 B1
(45) Date of Patent: Jul. 3, 2001

(54) HEMATOPOIETIC GROWTH FACTOR DERIVED FROM T LYMPHOCYTES

(76) Inventor: Chandra Choudhury, 1610 Robert E. Lee Blvd., New Orleans, LA (US) 70122

( * ) Notice: Subject to any disclaimer, the term of this patent is extended or adjusted under 35 U.S.C. 154(b) by 0 days.

(21) Appl. No.: 08/180,371

(22) Filed: Jan. 24, 1994

Related U.S. Application Data

(63) Continuation-in-part of application No. 07/906,866, filed on Jul. 1, 1992, now abandoned, which is a continuation-in-part of application No. 07/788,115, filed on Nov. 1, 1991, now abandoned, which is a continuation-in-part of application No. 07/747,784, filed on Aug. 19, 1991, now abandoned, which is a continuation-in-part of application No. 07/729,135, filed on Jul. 12, 1991, now abandoned, which is a continuation-in-part of application No. 07/356,006, filed on May 23, 1989, now abandoned.

(51) Int. Cl.[7] .......................... A61K 45/00; A61K 38/00; C07K 14/00; A01N 37/18
(52) U.S. Cl. ........................... 424/85.1; 435/69.1; 514/8; 514/12; 530/300; 530/350; 530/324; 530/351; 530/395
(58) Field of Search .......................... 514/8, 12; 530/350, 530/351, 395, 324, 300; 435/69.5; 424/85.1

(56) References Cited

U.S. PATENT DOCUMENTS

| 4,415,732 | 11/1983 | Caruthers et al. . |
| 4,438,032 | 3/1984 | Golde et al. . |
| 4,500,707 | 2/1985 | Caruthers et al. . |
| 4,810,643 | * 3/1989 | Souza ..................................... 435/68 |

FOREIGN PATENT DOCUMENTS

| 0 118 915 | 9/1984 | (EP) . |
| 0 261 592 | 3/1988 | (EP) . |
| 0 299 206 | 1/1989 | (EP) . |
| 0 299 782 | 1/1989 | (EP) . |
| 0 399 777 | 11/1990 | (EP) . |

OTHER PUBLICATIONS

Scopes, R.K. (1982) *Protein Purification*, New York: Springer–Verlag; pp. 111–117.*
Abrams et al., "Development of Rat Anti–Mouse Interleukin 3 Monoclonal Antibodies which Neutralize Bioactivity In Vitro," *J. Immunol.*, 140(1):131–137 (Jan. 1, 1988).
Balland et al., "Use of synthetic oligonucleotides in gene isolation and manipulation," *Biochimie*, 67:725–736 (1985).
Berger and Pizzo, "Preparation of Polyethylene Glycol–Tissue Plasminogen Activator Adducts That Retain Functional Activity: Characteristics and Behavior in Three Animal Species," *Blood*, 71(6):1641–1647 (Jun., 1988).
Bitter and Egan, "Expression of heterologous genes in *Saccharomyces crevisiae* from vectors utilizing the glyceralde–hyde–3–phosphate dehydrogenase gene promoter," *Gene*, 32:263–274 (1984).

Bleackley et al., "Translation of lymphocyte mRNA for mouse colony stimulating factor," *Nucleic Acids Research*, 11(10):3027–3035 (1983).
Bullock et al., "XL1–Blue: A High Efficiency Plasmid Transforming recA *Escheria coli* Strain With Beta–Galactosidase Selection," *Biotechniques*, 5(4):376–379 (1987).
Cepko et al., "Construction and Applications of a Highly Transmissible Murine Retrovirus Shuttle Vector," *Cell*, 37:1053–1062 (1984).
Chang et al., "Solid–Phase Peptide Synthesis Using Mild Base Cleavage of Nα–Flourenylmethyloxycarbonylamino Acids, Exemplified by a Synthesis of Dihydrosomatostatin," *Int. J. Pept. Protein Res.*, 11:246–249 (1978).
Davignon et al., "Selective production of interleukin 3 (IL 3) and granulocyte–macrophage colony–stimulating factor (GM–CSF) in vitro by murine L3T4+ T cells: lack of spontaneous IL 3 and GM–CSF production by Ly-2−/L3T4− lpr subset," *Eur. J. Immunol.*, 18(9):1367–1372 (1988).
Edge et al., "Total synthesis of a human leukocyte interferon gene," *Nature*, 292:756–762 (Aug. 20, 1981).
Fairchild et al., "T Cell–Derived Glucosteroid Response- -Modifying Factor ($GRMF_T$); A Unique Lymphokine Made By Normal T Lymphocytes and a T Cell Hybridoma," *J. Immunol.*, 132(2):821–827 (Feb., 1984).
Ferretti et al., "Total synthesis of a gene for bovine rhodopsin," *Proc. Natl. Acad. Sci. (USA)*, 83:599–603 (Feb., 1986).
Fung et al., "Molecular cloning of cDNA for murine interleukin–3," *Nature*, 307:233–237 (Jan. 19, 1984).
Gorman et al., "Recombinant Genomes Which Express Chloramphenicol Acetytransferase in Mammalian Cells," *Mol. Cel. Biol.*, 2(9):1044–1051 (Sep., 1982).
Gough et al., "Molecular cloning of cDNA encoding a murine hematopoietic growth regulator, granulocyte–macrophge colony stimulating factor," *Nature*, 309:763–767 (Jun. 28, 1984).
Graham and Van Der Eb, "A New Technique for the Assay of Infectivity of Human Adenovirus 5 DNA," *Virology*, 52:456–467 (1973).

(List continued on next page.)

Primary Examiner—Gary L. Kunz
Assistant Examiner—Robert S. Landsman
(74) *Attorney, Agent, or Firm*—Marshall, O'Toole, Gerstein, Murray & Borun

(57) ABSTRACT

A T cell-derived colony stimulating factor ("TC-CSF") may be isolated from media conditioned with T lymphocyte cells. TC-CSF stimulates formation of colonies composed of granulocytes, macrophages, megakaryocytes, fibrocytic stromal cells, lymphocytes, and mixed colonies of granulocytes and macrophages. Anion exchange chromatography may be employed in conjunction with gel filtration and rpHPLC to isolate TC-CSF. Human TC-CSF and murine TC-CSF cDNA, MRNA, genomic DNA nucleotide and amino acid sequences, expression products, pharmaceutical formulations and antibody materials are specifically provided.

4 Claims, 7 Drawing Sheets

OTHER PUBLICATIONS

Greenberger et al., "Production of Colony–stimulating Factor(s) for Granulocyte–Macrophage and Multipotential (Granulocyte/Erythoid/Megakaryocyte/Macrophage) Hematopoietic Progenitor Cells (CFU–GEMM) by Clonal Lines of Human IL–2–dependant T–lymphocytes," *Exp. Hematol.*, 12:720–727 (1984).

Hopp et al., "Prediction of protein antigenic determinants from amino acid sequences," *Proc. Natl. Acad. Sci.* (*USA*), 78(6):3824–3828 (Jun., 1981).

Hudson, "Methodological Implications of Simultaneous Solid–Phase Peptide Synthesis" *J. Org. Chem.*, 53:617–626 (1988).

Jerne, "The Immune System," *Scientific American*, 52–60 (Jul. 1973).

Kennedy et al., "Anti–idiotypes and Immunity," *Scientific American*, 48–56 (Jul. 1986).

Kennedy et al., "Anti–Idiotype Antibody Vaccine for Type B Viral Hepatitis in Chimpanzees," *Science*, 232:220–223 (1986).

Kern et al., "Identification of a Unique T Cell–Derived Lymphokine that Primes Macrophages for Tumor Cytotoxicity," J. Immunol., 143(12):4308–4316 (Dec. 15, 1989).

Kohler, "The Technique of Hybridoma Production," *Immunological Methods*, eds. Lefkovits et al., Academic Press, New York, NY (1979).

Kohler et al., "Continuous cultures of fused cells secreting antibody of predefined specificity," *Nature*, 256:495 (Aug. 7, 1975).

Kozak, "Compilation and analysis of sequences upstream from the translational start site in eukaryotic mRNAs," *Nucleic Acid Res.*, 12(2):857–872 (1984).

Kupper et al., "Growth of an Interleukin 2/Interleukin 4–Dependant T Cell Line Induced by Granulocyte–Macrophage Colony–Stimulating Factor (GM–CSF)," *J. Immunol.*, 138(12):4288–4292 (Jun. 15, 1987).

Lerner, "Tapping the immunological repertoire to produce antibodies of predetermined specificity," *Nature*, 299:592–596 (Oct. 14, 1982).

Malek et al., "The Murine IL 2 Receptor II," *J. Immunol.*, 133(4):1976–1982 (Oct., 1984).

Mann, "Molecular tectonics in biomineralization and biominimetic materials chemistry," *Nature*, 365:499–505 (Oct. 7, 1993).

Marx, "Making Antibodies Without the Antigens," *Science*, 228:162–165 (1985).

Metcalf, "The molecular control of cell division, differentiation commitment and maturation in hemopoietic cells," Nature, 339:27–30 (May 4, 1989).

Mochizuki et al., "Development and Characterization of Antiserum to Murine Granulocyte–Macrophage Colony––Stimulating Factor," *J. Immunol.*, 136(10):3706–3709 (May 15, 1986).

Mosmann et al., "Two Types of Murine Helper T Cell Clone," *J. Immunol.*, 136(7):2348–2357 (Apr., 1986).

Niman et al, "Generation of protein–reactive antibodies by short peptides is an event of high frequency: Implications for the structural basis of immune recognition," *Proc. Natl. Acad, Sci.* (*USA*), 80:4949–4953 (Aug., 1983).

Novotny et al., "Antigenic determinants in proteins coincide with surface regions accessbile to large probes (antibody domains)," *Proc. Natl. Acad. Sci.* (*USA*), 83:226–230 (Jan., 1986).

Occhionero et al., "Functional Characterization of Lymphokines From the EL–4 T Cell Line that Activate Macrophages for Nonspecific Tumor Cytotoxicity," *J. Leukocyte Biol.*, 35:405–414 (1984).

Ohara and Paul, "Production of a monoclonal antibody to and molecular characterization of B–cell stimulatory factor–1," *Nature*, 315:333–336 (May, 1985).

Ortega et al., "The Murine IL 2 Receptor I," *J. Immunol.*, 133(4):1970–1975 (Oct., 1984).

Oster et al., "Production of macrophage–, granulocyte–, granulocyte–macrophage–and multi–colony–stimulating factor by peripheral blood cells," *Eur. J. Immunol.*, 19:543–547 (1989).

Owhashi and Nawa, "Granulocyte–Macrophage Colony––Stimulating Factor Produced by Splenic T Lymphocytes of Mice Infected with *Schistosoma japonicum,*" *Infection and Immunity*, 51(1):213–217 (Jan., 1986).

Sanger et al., "DNA sequencing with chain–terminating inhibitors," *Proc. Natl. Acad. Sci.* (*USA*), 74(12):5463–5467 (Dec., 1977).

Sproat et al., "Chemical synthesis of a gene for somatomedin C," *Nucleic Acid Res.*, 13(8):2959–2977 (1985).

Stanley et al., "The structure and expression of the murine gene encoding granulocyte–macrophage colony stimulating factor: evidence for utilization of alternative promoters," *EMBO J.*, 4(10):2569–2573 (1985).

Tagaya et al., "ATL–derived factor (ADF), an IL–2 receptor/Tac inducer homologous to thioredoxin; possible involvement of dithiol–reduction in the IL–2 receptor induction," *The EMBO Journal*, 8(3):757–764 (1989).

Van Regenmortel, "Antigenic cross–reactivity between proteins and peptides: new insights and applications," *Trends Biochem. Sci.*, 12:237–240 (Jun., 1987).

Vieira and Messing, "The pUC plasmids, and M13mp7–derived system for insertion mutations and sequencing with synthetic universal primers," *Gene*, 19:259–268 (1982).

Wollman et al., "Cloning and Expression of a cDNA for Human Thioredoxin," *J. Biol. Chem.*, 263(30):15506–15512 (Oct. 25, 1988).

Yokota et al., "Isolation and characterization of lymphokine cDNA clones encoding mouse and human IgA–enhancing factor and eosinophil colony–stimulating factor activities: Relationship to interleukin 5," *Proc. Natl. Acad. Sci.*(*USA*), 84:7388–7392 (Nov., 1987).

Young et al., "Efficient isolation of genes by using antibody probes," *Proc. Natl. Acad. Sci.* (*USA*), 80:1194–1198 (Mar., 1983).

* cited by examiner

```
1   GAATTCCGCT CCTATGCGCC TCATTAGACA CACCAGTGCC TGAAAAGCTT CTTTATACGT    60
61  TCTATTCCCA ACTCCCCTTT TCCCCTATTT TCTCTTTCAT CTATTTTTCA ATATCATCTA   120
121 TTTTTTCATA CGGGAAGGAG TATGTTAAAA ATGACTCAGA GTCTCAAACA TGCTATGCAG   180
181 ACACTCTACC ACTGAGCTAT CTCCACGTGC TTAAATCTAA TTTAGTCATT AAGCAGCCCC   240
241 GACAAAGACA AATCTATTCT GGTCAATGTT TCCAAGGACC TTCACAATCC TCAGGCAAGC   300
301 GATTACCATC CTCATTTCTG ACCTGTTCGC ATATTTGCCA CAGTCAATTGT CTGATTCGG   360
361 AGAGTTGGAC TTATCAAGCT GAAAAAGATG AGCAGGACAC CCTTGGTATC TTGTCATCAT   420
421 GTAGTTCTGA CTTAGTCTGT CTAGGTGGAA TCAGAGAGTC TAGCTTTCCA CTGATATACG   480
481 TGATGCTGAC CCATCGATCA CACTCAATAG CAAGACTCAA GGGCATTACA CACCTTGCTT   540
541 CCAGGTTTTC TTCTTCTACA GTTTTTTACA GTAAAGTTTT CCAAGCATGT CTTCTACTTA   600
```

FIG. 1

```
601  TAAAACTATT TGAGTATTTA TTATTACTTA TTCCAACCAC GTGGTTTGTC CCACAAAGCT  660
661  CCATGAGTTT AAGCATCATC TGTCTCTCAA AGCCTCTTAA AATTATAACT AAAACTTGGA  720
721  TATTTTTCCA AACTCTAGAC TTCTTCCTAC CTGGCACCTT CAATTGAACA  780
781  TCCAACAGAC TGCTTTTTCT CAATCTAACT CAACTCAACG CCAATTGATC TTCCTTTCAG  840
841  CCTACTTTGT GCGAAAGGGT TCCCTGTTAG CAACTCCATC ATTCAAATCA CTTAGGCTCC  900
901  AAACACTGCA ATCAGATTTG ATGGGAACTT TTTTTTTTCC CAAAACTTCA ACTGTGTCCC  960
961  ATCTGGATTC CTGCATTAAT TTTAAAAAAC ACCATTCTTA TGCTTACTCT TTTCATGCCC  1020
1021 AACTGATCTT TCCGTAACAG AATACCCAAG GTATTTTAGG TAGAGTCATG AATGTCAATA  1080
1081 GTTCAGCCAA AACCCCTGTT ACAGAGAAAA AAAAATCACC CTTTACAGTG AGCTTTGAGA  1140
1141 CTTTGTGTGA TACAATTAAA GTGCCCTTTC AAAACATTTT CTGGTTCAGT GTGACAGAAT  1200
```

FIG. 1 (cont.)

```
1201 CATCCCATCA GACTCTTTCT ACCTTTGAAC CCAGACTTTA ATAGACCTTT TTCCAGAAAC 1260
1261 ACTATCTTTA ATTCATCTGT TTGGTGACGT CTCCCTTAAG TCTCTGCTCT GATTTCATCT 1320
1321 TCAAAATGAA GTCCCCTCAT GAGCCTTCTT TCTGGCACTG TTGCTTGCTG CCTAATCCTG 1380
1381 CTTCCCCTAA AGCTTCTCCA CCTTTATCTT CTCCATACCA CCAATCAATT TCTCAAGACT 1440
1441 GGATAGCCGA CTCTCTTTGC ATTCTAGTGC ATTGTTTATT TATGTGTAAG TGCGGAGTCCC 1500
1501 AAAAGACCAC CAAGGGGCTG ATTCTAGTGC AATCACACAA GGGTCTTTAC CCAAGCTGGA 1560
1561 GCTTGGGCTC TCCACTGACC CTGACTCAGC AAGACCTGAA GGTGGAGCCC CACCCAGTTT 1620
1621 CAAGCAAACG TTTATAGGGG TAAGCAATCA AGCAAGAGTG TTTTTAGCCT GATACACATT 1680
1681 TGATTGGGTGG TCTATTATGG AATTTTGTTG CCCTTTAAAA TAATTGGCTG CTGCTGGGAG 1740
1741 CCAAACCATA AGTTTAACTT CTGCTTTCCT CCTGATTGGT GGTTGTCAGG AAGTGAAGAG 1800
```

FIG. 1 (cont.)

```
      ----;----+----;----+----;----+----;----+----;----+----;----+
1801  CCAGGTACAG TAACGGAGAC ACAGGTTTGT TTGGGAGTAA ACATGGAAAC TGGTGCTAAA  1860
1861  CCCACTCCTC CCCCCAGCTT GGCTTGATGG TTAACTCAGT TCAACTTTAG GTCAGGTTCT  1920
1921  CTAAGATGGA GTCTGACTCC AGGATCTGGT CTCTCAGTGA GCACAGTTGC TTCCGAGACA  1980
1981  GGCTTTACAG TAAACACATA GGCATCACTC TAGGGCCAAG GGACAAAGAA GCAAAGTCCT  2040
2041  CCAGATTAAT TCTTCATTGT ATTAATAACC ATGGTGATTG TTAAATCGGA TGCCCTGACA  2100
      ----;----+----;----+----;----+----;----+----;----+----;----+
2101  GGTCTTCGCC AAACAGTATG CTCTGAACCT TTAGATCACG TTCCAGTTGC TAATACTCAG  2160
2161  TGTTGATGAT AGCACTGACT ACTGTCTGGC ATCTGAGAGT TTGCTGTGTT TGCTTGCGT   2220
2221  CTTCCCTATT CTAAATATCT CATTGAAGGT TTGCTGTGTT TGCTTGCGT  TTCCTGTTGC   2280
2281  CTTAAAGAGA GAGTTAGTTA GTTTGAAACA TGCCCCATCA CATGCTAGAT AAATGTATCC  2340
2341  AGTTCTTACC GACTGCGAAA AATAAGATGA TAGTCTTCCG AAAATTTTT CCCATGAAAT   2400
```

FIG. 1 (cont.)

```
2401  ATGAAAATTT AAATTTAGCT GAAATGTTTG TAGGTTTTGA AGAGTGTTCT GCTGGGGAGA  2460
2461  CTTCCCCCAG CTCCCTTTTC AGGTACTTCG GTCGGCCGAA AATTTAGGGC AAAATCTGCC  2520
2521  ATTAAAATTC GAGGTCTTCT CCGGTTGATG GCTTTGAATA C                      2561
```

FIG. 1 (cont.)

```
001  TTATGTCTTATATTTTATATTTTTGTAAATTAAAAAATTACAAGTTTTA   50
051  AATAGCCAATGGCTGGTTATGTTTTCAGAAAACATGATTAGACTAATTCA  100
101  TTAATGGTGGCTTCAAGCTTTTCCTTATTGGCTCCAGAAAATTCACCCAC  150
151  CTTTGTCCCTTCTTAAAAAAACTGGAATGTTGGCATGCATTTGACTTCAC  200
201  ACTCTGAAGCAAACATCCTGACAGTCATCCACATCTACTTCAAGGAATATC 250
251  ACGTTGGAATACTTTTCAGAGAGGGAATGAAAGAAAGGCTTGATCATTTT  300
301  GCAAGGCCCACACCACGTGGCTGAGAAGTCAACTACTACAAGTTTATCAC  350
351  CTGCAGCGTCCAAGGCTTCCTGAAAAGCAGTCTTCTGCTCTCGATCTGCTTC 400
401  ACCATCTTGGCTGCTGAGAGTCTGACGAGCGGTGTAAGGACGACGGAAAA  450
451  TGGATCCAAAGCACCAAACAGAGCTGGTGTTTTTTTCCATACAGGTG     500
501  AGTTACTATTGTAAAATAAATAATTTTAATTACAAAGGTCCAGTACCAA   550
551  TAGATATCTAAGAAATGTATAATTTGCCTCCAATAACAAACTTGTGCTTT  600
601  GATATTTTTATCATAAAAACTGAGTTTTC                      630
```

FIG. 2

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
        (A) LENGTH: 2561 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

```
GAATTCCGCT CCTATGCGCC TCATTAGACA CACCAGTGCC TGAAAAGCTT CTTTATACGT      60

TCTATTCCCA ACTCCCCTTT TCCCCTATTT TCTCTTTCAT CTATTTTTCA ATATCATCTA     120

TTTTTTCATA CGGGAAGGAG TATGTTAAAA ATGACTCAGA GTCTCAAACA TGCTATGCAG     180

ACACTCTACC ACTGAGCTAT CTCCACGTGC TTAAATCTAA TTTAGTCATT AAGCAGCCCC     240

GACAAAGACA AATCTATTCT GGTCAATGTT TCCAAGGACC TTCACAATCC TCAGGCAAGC     300

GATTACCATC CTCATTTCTG ACCTGTTCGC ATATTTGCCA CAGTCAATTG TCTGATTCGG     360

AGAGTTGGAC TTATCAAGCT GAAAAAGATG AGCAGGACAC CCTTGGTATC TTGTCATCAT     420

GTAGTTCTGA CTTAGTCTGT CTAGGTGGAA TCAGAGAGTC TAGCTTTCCA CTGATATACG     480
```

-continued

```
TGATGCTGAC CCATCGATCA CACTCAATAG CAAGACTCAA GGGCATTACA CACCTTGCTT    540

CCAGGTTTTC TTCTTCTACA GTTTTTTACA GTAAAGTTTT CCAAGCATGT CTTCTACTTA    600

TAAAACTATT TGAGTATTTA TTATTACTTA TTCCAACCAC GTGGTTTGTC CCACAAAGCT    660

CCATGAGTTT AAGCATCATC TGTCTCTCAA AGCCTCTTAA AATTATAACT AAAACTTGGA    720

TATTTTTCCA AACTCTAGAC TTCCAACGAC TTCTTCCTAC CTGGCACCTT CAATTGAACA    780

TCCAACAGAC TGCTTTTTCT CAATCTAACT CAACTCAACG CCAATTGATC TTCCTTTCAG    840

CCTACTTTGT GCGAAAGGGT TCCCTGTTAG CAACTCCATC ATTCAAATCA CTTAGGCTCC    900

AAACACTGCA ATCAGATTTG ATGGGAACTT TTTTTTTTCC CAAAACTTCA ACTGTGTCCC    960

ATCTGGATTC CTGCATTAAT TTTAAAAAAC ACCATTCTTA TGCTTACTCT TTTCATGCCC   1020

AACTGATCTT TCCGTAACAG AATACCCAAG GTATTTTAGG TAGAGTCATG AATGTCAATA   1080

GTTCAGCCAA AACCCTGTT ACAGAGAAAA AAAAATCACC CTTTACAGTG AGCTTTGAGA   1140

CTTTGTGTGA TACAATTAAA GTGCCCTTTC AAAACATTTT CTGGTTCAGT GTGACAGAAT   1200

CATCCCATCA GACTCTTTCT ACCTTTGAAC CCAGACTTTA ATAGACCTTT TTCCAGAAAC   1260

ACTATCTTTA ATTCATCTGT TTGGTGACGT CTCCCTTAAG TCTCTGCTCT GATTTCATCT   1320

TCAAAATGAA GTCCCCTCAT GAGCCTTCTT TCTGGCACTG TTGCTTGCTG CCTAATCCTG   1380

CTTCCCCTAA AGCTTCTCCA CCTTTATCTT CTCCATACCA CCAATCAATT TCTCAAGACT   1440

GGATAGCCGA CTCTCTTTGC TGTTCTATTT ATTGTTTATT TATGTGTAAG TGCGAGTCCC   1500

AAAAGACCAC CAAGGGGCTG ATTCTAGTGC AATCACACAA GGGTCTTTAC CCAAGCTGGA   1560

GCTTGGGCTC TCCACTGACC CTGACTCAGC AAGACCTGAA GGTGGAGCCC CACCCAGTTT   1620

CAAGCAAACG TTTATAGGGG TAAGCAATCA AGCAAGAGTG TTTTTAGCCT GATACACATT   1680

TGATTGGTGG TCTATTATGG AATTTTGTTG CCCTTTAAAA TAATTGGCTG CTGCTGGGAG   1740

CCAAACCATA AGTTTAACTT CTGCTTTCCT CCTGATTGGT GGTTGTCAGG AAGTGAAGAG   1800

CCAGGTACAG TAACGGAGAC ACAGGTTTGT TTGGGAGTAA ACATGGAAAC TGGTGCTAAA   1860

CCCACTCCTC CCCCCAGCTT GGCTTGATGG TTAACTCAGT TCAACTTTAG GTCAGGTTCT   1920

CTAAGATGGA GTCTGACTCC AGGATCTGGT CTCTCAGTGA GCACAGTTGC TTCCGAGACA   1980

GGCTTTACAG TAAACACATA GGCATCACTC TAGGGCAAG GGACAAAGAA GCAAAGTCCT   2040

CCAGATTAAT TCTTCATTGT ATTAATAACC ATGGTGATTG TTAAATCGGA TGCCCTGACA   2100

GGTCTTCGCC AAACAGTATG CTCTGAACCT TTAGATCACG TTCCAGTTGC TAATACTCAG   2160

TGTTGATGAT AGCACTGACT ACTGTCTGGC ATCTGAGAGT TCCCTGCCCT TAGCAGTTTG   2220

CTTCCCTATT CTAAATATCT CATTGAAGGT TTGCTGTGTT TTGCTTGCGT TTCCTGTTGC   2280

CTTAAAGAGA GAGTTAGTTA GTTTGAAACA TGCCCCATCA CATGCTAGAT AAATGTATCC   2340

AGTTCTTACC GACTGCGAAA AATAAGATGA TAGTCTTCCG AAAATTTTTT CCCATGAAAT   2400

ATGAAAATTT AAATTTAGCT GAAATGTTTG TAGGTTTTGA AGAGTGTTCT GCTGGGGAGA   2460

CTTCCCCCAG CTCCCTTTTC AGGTACTTCG GTCGGCCGAA AATTTAGGGC AAAATCTGCC   2520

ATTAAAATTC GAGGTCTTCT CCGGTTGATG GCTTTGAATA C                      2561
```

(2) INFORMATION FOR SEQ ID NO: 2:

(i) SEQUENCE CHARACTERISTICS:
        (A) LENGTH: 554 amino acids
        (B) TYPE: amino acid
        (D) TOPOLOGY: linear (ii) MOLECULE TYPE: protein (xi) SEQUENCE DESCRIPTION: SEQ ID NO: 2:

Met Pro Leu Leu Cys Ala Ser Leu Asp Thr Pro Val Pro Glu Lys Leu
1               5                   10                  15

Leu Tyr Thr Phe Tyr Ser Gln Leu Pro Phe Ser Pro Ile Phe Ser Phe
            20                  25                  30

Ile Tyr Phe Ser Ile Ser Ser Ile Phe Ser Tyr Gly Lys Glu Tyr Val
        35                  40                  45

Lys Asn Asp Ser Glu Ser Gln Thr Cys Tyr Ala Asp Thr Leu Pro Leu
    50                  55                  60

Ser Tyr Leu His Val Leu Lys Ser Asn Leu Val Ile Lys Gln Pro Arg
65                  70                  75                  80

Gln Arg Gln Ile Tyr Ser Gly Gln Cys Phe Gln Gly Pro Ser Gln Ser
                85                  90                  95

Ser Gly Lys Arg Leu Pro Ser Ser Phe Leu Thr Cys Ser His Ile Cys
            100                 105                 110

His Ser Gln Leu Ser Asp Ser Glu Ser Trp Thr Tyr Gln Ala Glu Lys
        115                 120                 125

Asp Glu Gln Asp Thr Leu Gly Ile Leu Ser Ser Cys Ser Ser Asp Leu
    130                 135                 140

Val Cys Leu Gly Gly Ile Arg Glu Ser Ser Phe Pro Leu Ile Tyr Val
145                 150                 155                 160

Met Leu Thr His Arg Ser His Ser Ile Ala Arg Leu Lys Gly Ile Thr
                165                 170                 175

His Leu Ala Ser Arg Phe Ser Ser Thr Val Phe Tyr Ser Lys Val
        180                 185                 190

Phe Gln Ala Cys Leu Leu Leu Ile Lys Leu Phe Glu Tyr Leu Leu Leu
        195                 200                 205

Leu Ile Pro Thr Thr Trp Phe Val Pro Gln Ser Ser Met Ser Leu Ser
    210                 215                 220

Ile Ile Cys Leu Ser Lys Pro Leu Lys Ile Ile Thr Lys Thr Trp Ile
225                 230                 235                 240

Phe Phe Gln Thr Leu Asp Phe Gln Arg Leu Leu Pro Thr Trp His Leu
                245                 250                 255

Gln Leu Asn Ile Gln Gln Thr Ala Phe Ser Gln Ser Asn Ser Thr Gln
            260                 265                 270

Arg Gln Leu Ile Phe Leu Ser Ala Tyr Phe Val Arg Lys Gly Ser Leu
        275                 280                 285

Leu Ala Thr Pro Ser Phe Lys Ser Leu Arg Leu Gln Thr Leu Gln Ser
    290                 295                 300

Asp Leu Met Gly Thr Phe Phe Pro Lys Thr Ser Thr Val Ser His
305                 310                 315                 320

Leu Asp Ser Cys Ile Asn Phe Lys Lys His His Ser Tyr Ala Tyr Ser
                325                 330                 335

Phe His Ala Gln Leu Ile Phe Pro Xaa Gln Asn Thr Gln Gly Ile Leu
            340                 345                 350

Gly Arg Val Met Asn Val Asn Ser Ser Ala Lys Thr Pro Val Thr Glu
        355                 360                 365

Lys Lys Lys Ser Pro Phe Thr Val Ser Phe Glu Thr Leu Cys Asp Thr
    370                 375                 380

Ile Lys Val Pro Phe Gln Asn Ile Phe Trp Phe Ser Val Thr Glu Ser
385                 390                 395                 400

Ser His Gln Thr Leu Ser Thr Phe Glu Pro Arg Leu Xaa Xaa Thr Phe

-continued

```
                        405                 410                 415
Phe Gln Lys His Tyr Leu Xaa Phe Ile Cys Leu Val Thr Ser Pro Leu
            420                 425                 430
Ser Leu Cys Ser Asp Phe Ile Phe Lys Met Lys Ser Pro His Glu Pro
            435                 440                 445
Ser Phe Trp His Cys Cys Leu Leu Pro Asn Pro Ala Ser Pro Lys Ala
    450                 455                 460
Ser Pro Pro Leu Ser Ser Pro Tyr His Gln Ser Ile Ser Gln Asp Trp
465                 470                 475                 480
Ile Ala Asp Ser Leu Cys Cys Ser Ile Tyr Cys Leu Phe Met Cys Lys
                485                 490                 495
Cys Glu Ser Gln Lys Thr Thr Lys Gly Leu Ile Leu Val Gln Ser His
            500                 505                 510
Lys Gly Leu Tyr Pro Ser Trp Ser Leu Gly Ser Pro Leu Thr Leu Thr
            515                 520                 525
Gln Gln Asp Leu Lys Val Glu Pro His Pro Val Ser Ser Lys Arg Leu
530                 535                 540
Xaa Gly Xaa Ala Ile Lys Gln Glu Cys Phe
545                 550
```

(2) INFORMATION FOR SEQ ID NO: 3:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Pro Asn Leu Gly Ile Phe Ala Asx Thr Met Pro Glu Asp Ala Gly
1               5                   10                  15
Asn Ser Val
```

(2) INFORMATION FOR SEQ ID NO: 4:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 4:

```
Asp Thr Met Pro Glu Asn
1               5
```

(2) INFORMATION FOR SEQ ID NO: 5:

(i) SEQUENCE CHARACTERISTICS:
        (A) LENGTH: 630 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..630

(xi) SEQUENCE DESCRIPTION: SEQ ID NO: 5:

```
GAA AAC TCA GTT TTT ATG ATA AAA AAT ATC AAA GCA CAA GTT TGT TAT        48
```

```
Glu Asn Ser Val Phe Met Ile Lys Asn Ile Lys Ala Gln Val Cys Tyr
  1               5                  10                  15

TGG AGG CAA ATT ATA CAT TTC TTA GAT ATC TAT TGG TAC TGG ACC TTT        96
Trp Arg Gln Ile Ile His Phe Leu Asp Ile Tyr Trp Tyr Trp Thr Phe
             20                  25                  30

GTA ATT AAA ATT AAT TTA TTT TAC AAT AGT AAC TCA CCT GTA TGG AAA       144
Val Ile Lys Ile Asn Leu Phe Tyr Asn Ser Asn Ser Pro Val Trp Lys
             35                  40                  45

AAA AAA CAA CCA GCT CTG TTT GGT GCT TTG GAT CCA TTT CCG TCG GTC       192
Lys Lys Gln Pro Ala Leu Phe Gly Ala Leu Asp Pro Phe Pro Ser Val
     50                  55                  60

CTT ACA GCC GCT CGT CAG ACT CCA GCA GCC AAG ATG GTG AAG CAG ATC       240
Leu Thr Ala Ala Arg Gln Thr Pro Ala Ala Lys Met Val Lys Gln Ile
 65                  70                  75                  80

GAG AGC AAG ACT GCT TTT CAG GAA GCC TTG GAC GCT GCA GGT GAT AAA       288
Glu Ser Lys Thr Ala Phe Gln Glu Ala Leu Asp Ala Ala Gly Asp Lys
                 85                  90                  95

CTT GTA GTA GTT GAC TTC TCA GCC ACG TGG TGT GGG CCT TGC AAA ATG       336
Leu Val Val Val Asp Phe Ser Ala Thr Trp Cys Gly Pro Cys Lys Met
            100                 105                 110

ATC AAG CCT TTC TTT CAT TCC CTC TCT GAA AAG TAT TCC AAC GTG ATA       384
Ile Lys Pro Phe Phe His Ser Leu Ser Glu Lys Tyr Ser Asn Val Ile
            115                 120                 125

TTC CTT GAA GTA GAT GTG GAT GAC TGT CAG GAT GTT GCT TCA GAG TGT       432
Phe Leu Glu Val Asp Val Asp Asp Cys Gln Asp Val Ala Ser Glu Cys
130                 135                 140

GAA GTC AAA TGC ATG CCA ACA TTC CAG TTT TTT AAG AAG GGA CAA AAG       480
Glu Val Lys Cys Met Pro Thr Phe Gln Phe Phe Lys Lys Gly Gln Lys
145                 150                 155                 160

GTG GGT GAA TTT TCT GGA GCC AAT AAG GAA AAG CTT GAA GCC ACC ATT       528
Val Gly Glu Phe Ser Gly Ala Asn Lys Glu Lys Leu Glu Ala Thr Ile
                165                 170                 175

AAT GAA TTA GTC TAA TCA TGT TTT CTG AAA ACA TAA CCA GCC ATT GGC       576
Asn Glu Leu Val Xaa Ser Cys Phe Leu Lys Thr Xaa Pro Ala Ile Gly
            180                 185                 190

TAT TTA AAA CTT GTA ATT TTT TTA ATT TAC AAA AAT ATA AAA TAT AAG       624
Tyr Leu Lys Leu Val Ile Phe Leu Ile Tyr Lys Asn Ile Lys Tyr Lys
        195                 200                 205

ACA TAA                                                               630
Thr Xaa
    210

(2) INFORMATION FOR SEQ ID NO: 6:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO: 6:

Glu Asn Ser Val Phe Met Ile Lys Asn Ile Lys Ala Gln Val Cys Tyr
  1               5                  10                  15

Trp Arg Gln Ile Ile His Phe Leu Asp Ile Tyr Trp Tyr Trp Thr Phe
             20                  25                  30

Val Ile Lys Ile Asn Leu Phe Tyr Asn Ser Asn Ser Pro Val Trp Lys
             35                  40                  45

Lys Lys Gln Pro Ala Leu Phe Gly Ala Leu Asp Pro Phe Pro Ser Val
     50                  55                  60
```

```
Leu Thr Ala Ala Arg Gln Thr Pro Ala Ala Lys Met Val Lys Gln Ile
 65                  70                  75                  80

Glu Ser Lys Thr Ala Phe Gln Glu Ala Leu Asp Ala Ala Gly Asp Lys
             85                  90                  95

Leu Val Val Val Asp Phe Ser Ala Thr Trp Cys Gly Pro Cys Lys Met
            100                 105                 110

Ile Lys Pro Phe Phe His Ser Leu Ser Glu Lys Tyr Ser Asn Val Ile
            115                 120                 125

Phe Leu Glu Val Asp Val Asp Asp Cys Gln Asp Val Ala Ser Glu Cys
        130                 135                 140

Glu Val Lys Cys Met Pro Thr Phe Gln Phe Lys Lys Gly Gln Lys
145                 150                 155                 160

Val Gly Glu Phe Ser Gly Ala Asn Lys Glu Lys Leu Glu Ala Thr Ile
                165                 170                 175

Asn Glu Leu Val Xaa Ser Cys Phe Leu Lys Thr Xaa Pro Ala Ile Gly
            180                 185                 190

Tyr Leu Lys Leu Val Ile Phe Leu Ile Tyr Lys Asn Ile Lys Tyr Lys
            195                 200                 205

Thr Xaa
    210

(2) INFORMATION FOR SEQ ID NO: 7:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO: 7:

Tyr Trp Thr Phe Val Ile Lys Ile Asn Leu Phe Tyr Asn Ser Asn Ser
  1               5                  10                  15

Pro Val Trp Lys Lys Lys Gln Pro Ala Leu Phe Gly Ala Leu
             20                  25                  30

(2) INFORMATION FOR SEQ ID NO: 8:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO: 8:

Tyr Phe Val Ile Lys Ile Asn Leu Phe Tyr Asn Ser Asn Ser Pro Val
  1               5                  10                  15

Trp Lys Lys Lys Gln Pro Ala Leu Phe
             20                  25

(2) INFORMATION FOR SEQ ID NO: 9:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
```

(B) LOCATION: 2..97

(xi) SEQUENCE DESCRIPTION: SEQ ID NO: 9:

```
T TGG TAC TGG ACC TTT GTA ATT AAA ATT AAT TTA TTT TAC AAT AGT          46
  Trp Tyr Trp Thr Phe Val Ile Lys Ile Asn Leu Phe Tyr Asn Ser
   1               5                  10                  15

AAC TCA CCT GTA TGG AAA AAA AAA CAA CCA GCT CTG TTT GGT GCT TTG        94
Asn Ser Pro Val Trp Lys Lys Lys Gln Pro Ala Leu Phe Gly Ala Leu
             20                  25                  30

GAT                                                                    97
Asp
```

(2) INFORMATION FOR SEQ ID NO: 10:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO: 10:

```
Trp Tyr Trp Thr Phe Val Ile Lys Ile Asn Leu Phe Tyr Asn Ser Asn
 1               5                  10                  15

Ser Pro Val Trp Lys Lys Lys Gln Pro Ala Leu Phe Gly Ala Leu Asp
             20                  25                  30
```

(2) INFORMATION FOR SEQ ID NO: 11:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..311

(xi) SEQUENCE DESCRIPTION: SEQ ID NO: 11:

```
      CC TAC TTT GTG CGA AAG GGT TCC CTG TTA GCA ACT CCA TCA TTC       44
         Tyr Phe Val Arg Lys Gly Ser Leu Leu Ala Thr Pro Ser Phe
          1               5                  10

AAA TCA CTT AGG CTC CAA ACA CTG CAA TCA GAT TTG ATG GGA ACT TTT        92
Lys Ser Leu Arg Leu Gln Thr Leu Gln Ser Asp Leu Met Gly Thr Phe
 15                  20                  25                  30

TTT TTT CCC AAA ACT TCA ACT GTG TCC CAT CTG GAT TCC TGC ATT AAT       140
Phe Phe Pro Lys Thr Ser Thr Val Ser His Leu Asp Ser Cys Ile Asn
                 35                  40                  45

TTT AAA AAA CAC CAT TCT TAT GCT TAC TCT TTT CAT GCC CAA CTG ATC       188
Phe Lys Lys His His Ser Tyr Ala Tyr Ser Phe His Ala Gln Leu Ile
             50                  55                  60

TTT CCG TAA CAG AAT ACC CAA GGT ATT TTA GGT AGA GTC ATG AAT GTC       236
Phe Pro Xaa Gln Asn Thr Gln Gly Ile Leu Gly Arg Val Met Asn Val
         65                  70                  75

AAT AGT TCA GCC AAA ACC CCT GTT ACA GAG AAA AAA AAA TCA CCC TTT       284
Asn Ser Ser Ala Lys Thr Pro Val Thr Glu Lys Lys Lys Ser Pro Phe
     80                  85                  90

ACA GTG AGC TTT GAG ACT TTG TGT GAT                                   311
Thr Val Ser Phe Glu Thr Leu Cys Asp
 95                 100
```

(2) INFORMATION FOR SEQ ID NO: 12:

(i) SEQUENCE CHARACTERISTICS:
        (A) LENGTH: 103 amino acids
        (B) TYPE: amino acid
        (D) TOPOLOGY: linear (ii) MOLECULE TYPE: protein (xi) SEQUENCE DESCRIPTION: SEQ ID NO: 12:

```
Tyr Phe Val Arg Lys Gly Ser Leu Leu Ala Thr Pro Ser Phe Lys Xaa
 1               5                  10                  15
Leu Arg Leu Gln Thr Leu Gln Ser Asp Leu Met Gly Thr Phe Phe
                20                  25                  30
Pro Lys Thr Ser Thr Val Ser His Leu Asp Ser Cys Ile Asn Phe Lys
                35                  40                  45
Lys His His Ser Tyr Ala Tyr Ser Phe His Ala Gln Leu Ile Phe Pro
                50                  55                  60
Xaa Gln Asn Thr Gln Gly Ile Leu Gly Arg Val Met Asn Val Asn Ser
 65                  70                  75                  80
Ser Ala Lys Thr Pro Val Thr Glu Lys Lys Lys Ser Pro Phe Thr Val
                85                  90                  95
Ser Phe Glu Thr Leu Cys Asp
                100
```

(2) INFORMATION FOR SEQ ID NO: 13:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO: 13:

```
Phe Thr Val Ser
 1
```

(2) INFORMATION FOR SEQ ID NO: 14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO: 14:

```
Lys Lys Lys Gln Pro Ala
 1               5
```

(2) INFORMATION FOR SEQ ID NO: 15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO: 15:

```
Val Ile Lys Ile Asn Leu
 1               5
```

(2) INFORMATION FOR SEQ ID NO: 16:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO: 16:

```
Asn Ser Asn Ser Pro Val
1               5
```

(2) INFORMATION FOR SEQ ID NO: 17:

(i) SEQUENCE CHARACTERISTICS:
        (A) LENGTH: 630 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

```
TTATGTCTTA TATTTTATAT TTTTGTAAAT TAAAAAAATT ACAAGTTTTA AATAGCCAAT      60
GGCTGGTTAT GTTTTCAGAA AACATGATTA GACTAATTCA TTAATGGTGG CTTCAAGCTT     120
TTCCTTATTG GCTCCAGAAA ATTCACCCAC CTTTTGTCCC TTCTTAAAAA ACTGGAATGT     180
TGGCATGCAT TTGACTTCAC ACTCTGAAGC AACATCCTGA CAGTCATCCA CATCTACCTC     240
AAGGAATATC ACGTTGGAAT ACTTTTCAGA GAGGGAATGA AAGAAAGGCT TGATCATTTT     300
GCAAGGCCCA CACCACGTGG CTGAGAAGTC AACTACTACA AGTTTATCAC CTGCTGCGTC     360
CAAGGCTTCC TGAAAAGCAG TCTTGCTCTC GATCTGCTTC ACCATCTTGG CTGCTGGAGT     420
CTGACGAGCG GCTGTAAGGA CCGACGGAAA TGGATCCAAA GCACCAAACA GAGCTGGTTG     480
TTTTTTTTTC CATACAGGTG AGTTACTATT GTAAAATAAA TTAATTTTAA TTACAAAGGT     540
CCAGTACCAA TAGATATCTA AGAAATGTAT AATTTGCCTC CAATAACAAA CTTGTGCTTT     600
GATATTTTTT ATCATAAAAA CTGAGTTTTC                                     630
```

(2) INFORMATION FOR SEQ ID NO: 18:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO: 18:

```
Ala Cys Asn Ala Thr Gly Cys Cys Asn Gly Ala Pro Gly Ala Tyr Gly
1               5                   10                  15
Cys
```

HEMATOPOIETIC GROWTH FACTOR DERIVED FROM T LYMPHOCYTES

This is a continuation-in-part of U.S. Ser. No. 07/906,866, filed Jul. 1, 1992, now abandoned, which in turn is a continuation-in-part of U.S. Ser. No. 07/788,115, filed Nov. 1, 1991, now abandoned, which in turn is a continuation-in-part of U.S. Ser. No. 07/747,784, filed Aug. 19, 1991, now abandoned, which in turn is a continuation-in-part of U.S. Ser. No. 07/729,135, filed Jul. 12, 1991, now abandoned, which in turn is a continuation-in-part of U.S. Ser. No. 07/356,006, filed May 23, 1989, now abandoned, The present invention relates in general to colony stimulating factors and specifically relates to colony stimulating factors derived from T cells.

BACKGROUND

Mediators of proliferation and differentiation for hematopoietic progenitor cells of all lineages are frequently present in the same conditioned medium. Although these secreted growth factors have similar molecular mass [usually between 25 to 35 kilo Daltons ("Kd")] and may have apparently overlapping functional properties, they are products of distinct genes.

Hematopoietic growth factors include factors which stimulate development of certain hematopoietic cell lineages: IL-3, which has multi-lineage activity; GM-CSF, which predominantly stimulates granulocyte and macrophage colony formation, although, under certain conditions, it may stimulate megakaryocytic lineage cells as well; CSF-1, which stimulates only macrophage colonies; and G-CSF, which stimulates only granulocyte colony formation. None of these growth factors have a molecular mass ("IMW") exceeding about 30 Kd.

Hematopoietic growth factors may be used in treating immune-compromised patients, including Acquired Immunodeficiency Syndrome "AIDS" patients and certain types of cancer patients. Accordingly, it is desirable to obtain additional hematopoietic growth factors for existing and new applications.

SUMMARY OF THE INVENTION

The present invention provides a purified and isolated nucleic acid encoding a T cell colony stimulating factor ("TC-CSF"), which term is defined by a nucleotide sequence selected from the group consisting of: a nucleotide sequence encoding a TC-CSF (such as SEQ ID NO: 1) or the nucleotide sequence in SEQ ID NO: 5; a nucleotide sequence which encodes the sequence of amino acids of SEQ ID NO: 2, SEQ ID NO: 3, SEQ ID NO: 4, the amino acid sequence of SEQ ID NO: 5 or SEQ ID NO: 6; a nucleotide sequence which hybridizes under stringent conditions with any 20 sequential nucleotides encoding a sequence of amino acids in SEQ ID NO: 2, SEQ ID NO: 3, SEQ ID NO: 4, the amino acid sequence of SEQ ID NO: 5 or SEQ ID NO: 6, or with the complement thereof; a nucleotide sequence which hybridizes under stringent conditions with any 20 sequential nucleotides in a nucleic acid encoding a TC-CSF (such as SEQ ID NO: 1 or the nucleotide sequence in SEQ ID NO: 6) or with the complement thereof; and a nucleotide sequence which encodes an epitope encoded by 6 sequential amino acids in a TC-CSF or in the specific amino acid sequence of SEQ ID NO: 2, SEQ ID NO: 3, SEQ ID NO: 4 or SEQ ID NO: 6, and preferably SEQ ID NO:7, or SEQ ID NO: 8.

The present invention further provides a vector including a nucleic acid according to the present invention, and a cell, preferably a eukaryotic cell, including such a vector or including a nucleic acid according to the present invention at a location or in a multiplicity in which it does not occur in nature. Such a vector may be the eukaryotic cell vector deposited as ATCC Accession No. 68824 on Oct. 28, 1991, with the American Type Culture Collection, 12301 Parklawn Drive, Rockville, Md. 20852. Other vectors according to the present invention may be prokaryotic or eukaryotic expression vectors, including baculovirus vectors.

The present invention also provides an isolated polypeptide having a biological or immunological property of a T cell-derived colony stimulating factor and having an amino acid sequence in which at least 6 sequential amino acids are identical to 6 sequential amino acids in a TC-CSF, particularly wherein the polypeptide includes an epitope of TC-CSF in native or denatured conformation.

An isolated TC-CSF polypeptide according to the present invention may be selected from the group consisting of human TC-CSF, mouse TC-CSF, rat TC-CSF, bovine TC-CSF, canine TC-CSF, feline TC-CSF, ovine TC-CSF, ape TC-CSF, avian TC-CSF, and porcine TC-CSF, especially a TC-CSF having a molecular mass of about 2.5–3.5 Kd, about 11–13 Kd, about 20–23 Kd, about 25–30 Kd or about 55 Kd, and may include an amino acid sequence comprising a sequence of 6 or more amino acids in SEQ ID NO: 2, SEQ ID NO: 3, SEQ ID NO: 4, the amino acid sequence of SEQ ID NO: 5 or SEQ ID NO: 6, and preferably, SEQ ID NO:7 or SEQ ID NO: 8. The TC-CSF may be an expression product of a cell including a vector having DNA encoding TC-CSF or of a cell including a nucleic acid according to the present invention at a location or in a multiplicity in which it does not occur in nature. The isolated TC-CSF polypeptide may further include a diluent, adjuvant or carrier, preferably wherein the diluent comprises an isotonic buffer or pharmaceutical grade water for injection to form a pharmaceutical composition.

Any TC-CSF or nucleic acid according to the present invention not directly provided herein may be obtained according to procedures well known to those skilled in the art, including obtaining the screening of DNA libraries with polynucleotide probes based on the nucleotide sequences and deposited vector provided herein, and including identifying cells expressing TC-CSF by using a labeled antibody or oligonucleotide according to the present invention, isolating mRNA therefrom and preparing cDNA from the TC-CSF mRNA.

The isolated polypeptide may also include a label or reporter group or may be bound to a support. The isolated TC-CSF polypeptide according to the present invention may be associated with a support and an anti-TC-CSF antibody in a diagnostic kit for an immunoassay.

In addition, the present invention provides an isolated ligand specifically binding a TC-CSF, which ligand may be a TC-CSF receptor. Such a TC-CSF receptor may be identified using labeled TC-CSF according to the present invention and may be isolated using purified TC-CSF according to the present invention by techniques well known to those skilled in the art. Alternatively, the ligand may be serum or an isolated monoclonal or polyclonal antibody exhibiting a specific immunoreactivity with a TC-CSF, in particular exhibiting a specific immunoreactivity with an expression product of a cell containing a vector having DNA encoding a TC-CSF or a cell including a nucleic acid according to the present invention at a location or in a multiplicity in which it does not occur in nature.

A purified and isolated antigen is provided according to the present invention exhibiting immunological characteristics such that it specifically reacts with a monoclonal or polyclonal antibody against a TC-CSF, and the present invention also includes an immortalized cell line, such as a hybridoma, producing a monoclonal antibody to a TC-CSF.

A process for purifying TC-CSF according to the present invention includes the steps of applying cell culture supernatant containing TC-CSF to an anion exchange column, and collecting a fraction containing a TC-CSF from the anion exchange column, especially wherein the applying step includes the step of introducing the TC-CSF onto a column having a quaternary ammonium group bound to a support. The purification process may further include the steps of introducing the TC-CSF onto a gel filtration column and retaining fractions comprising TC-CSF. The purification process may also include the steps of: concentrating the eluate from the anion exchange column; introducing a TC-CSF-containing solution onto a rpHPLC column, and pooling fractions eluted therefrom; and dialyzing a TC-CSF containing solution.

A method for production of a T cell-derived colony stimulating factor (TC-CSF) according to the present invention includes the step of culturing a medium enriched in cells containing a gene encoding TC-CSF under conditions which permit expression of the gene and isolating TC-CSF from the medium or cells.

A method of treatment according to the present invention includes administering to a patient in need of therapy an effective amount of a pharmaceutical composition according to the present invention, and preferably includes administering to a patient in need of therapy an effective amount of a pharmaceutical composition including a human TC-CSF.

Also part of the present invention is a pharmaceutical composition which includes a TC-CSF, preferably a human TC-CSF. More preferably such composition comprises a pharmaceutically acceptable carrier such as isotonic aqueous buffer or pharmaceutical grade water for injection.

The pharmaceutical compositions according to the present invention may be formulated in accordance with standard procedures adapted for parenteral administration to humans. The compositions for intravenous administration are usually solutions of the sterile derivative of sterile isotonic aqueous buffer. Where necessary, the composition may also include a solubilizing agent. The composition may be supplied in unit dosage form, such as a dry powder or water-free concentrate in a sealed container such as an ampoule. For administration by infusion, the composition may be dispensed from an infusion bottle containing sterile pharmaceutical grade water for injection. For administration by injection, the composition may be dispensed from a vial of sterile water for injection. The injectable or infusible composition will be made up by mixing the ingredients prior to administration.

The effective amount of complex administered depends on many factors. The precise dose to be employed and the mode of administration may be decided according to the circumstances as determined by a physician.

According to the present invention, an anti-idiotypic antibody to a TC-CSF may be raised. Such an antibody may be used in place of a TC-CSF for certain applications.

Also according to the present invention an immunoassay may employ a TC-CSF or a TC-CSF ligand. A hybridization assay according to the present invention may employ a TC-CSF coding or non-coding sequence or a sequence complementary thereto. A primer extension assay according to the present invention may employ a TC-CSF coding or non-coding sequence or a sequence complementary thereto as primers. For immunoassays, hybridization assays and primer extension assays, the components of the assay may be provided in kit form.

BRIEF DESCRIPTION OF THE DRAWINGS

FIG. 1 is a nucleotide sequence SEQ ID NO:1 determined for a murine TC-CSF;

FIG. 2 is a nucleotide sequence SEQ ID NO:17 in reversed complementary form [i.e., the reverse (3'–5') form of the complement of the coding sequence] for a human TC-CSF.

DETAILED DESCRIPTION

Figure 3:
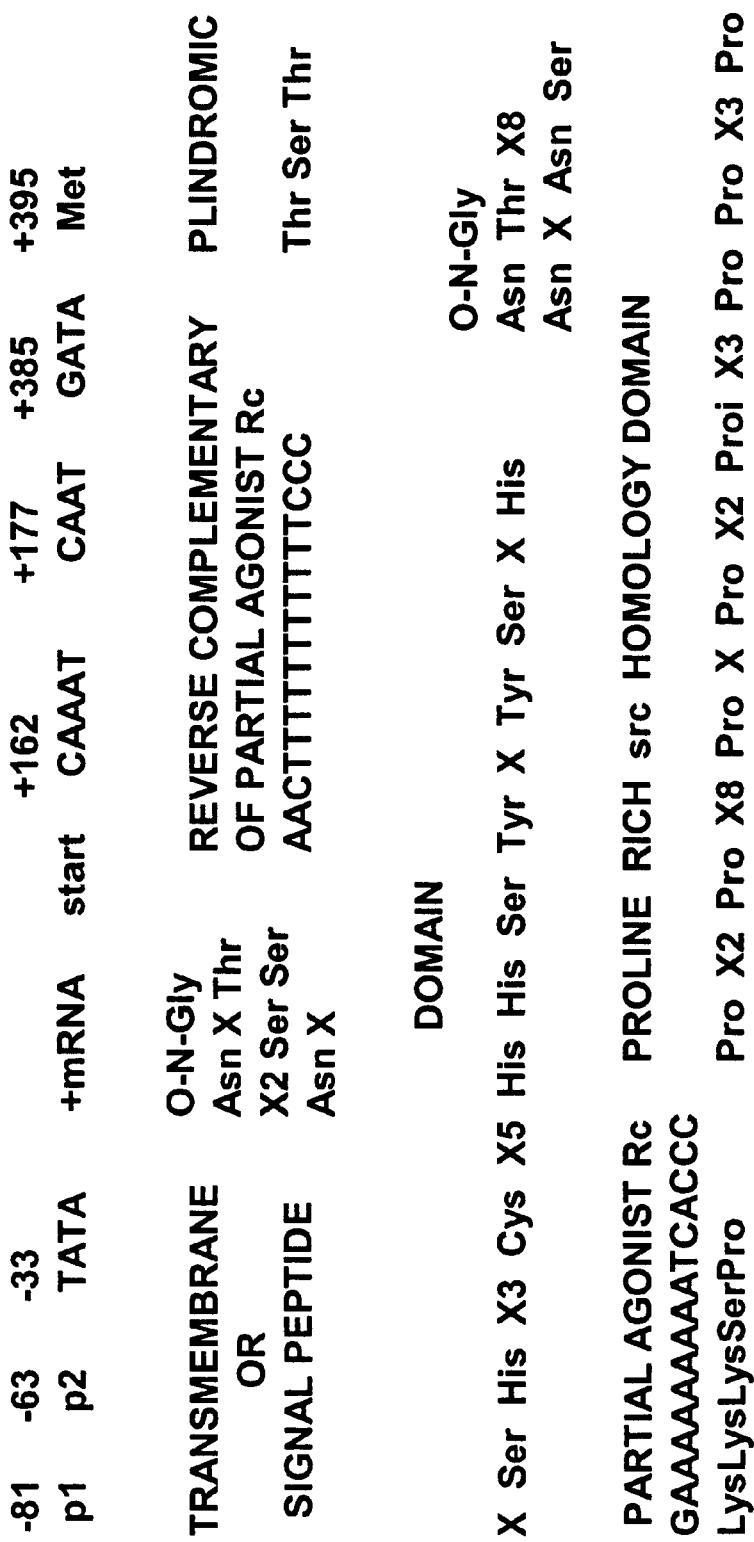
FIG. 3 is a schematic model for structural biology of clone CC2.

"Operably linked" as used herein refers to a structural connection which permits the normal function (as understood by those skilled in the art) of the components to be performed. Thus, a coding sequence is "operably linked" to a control sequence when the coding sequence is located on the same or a complementary DNA strand and its transcription is affected by the control of this sequence.

"Exogenous DNA" as used herein refers to DNA in a host cell in which it is not found in nature or under the control of a promoter to which it is not operably linked in nature or in a number of copies per cell which does not occur in nature.

As used herein, a medium is "enriched" in a kind of cell if it contains only that kind of cell or it contains a higher proportion of the kind of cell relative to other kinds of cells in the medium.

As used herein, the term "cell" includes progeny. Thus, "transformed cells" include a cell transformed with a vector and cells derived therefrom without regard for the number of cell division even though progeny may not be genetically identical due to deliberate or inadvertent mutations.

"Expression system" herein includes DNA encoding a polypeptide to be expressed operably linked to DNA controlling transcription of the DNA sequence, so that a host transformed with such DNA expresses the encoded polypeptides. The expression system include a vector called an "expression vector" or may be integrated into the host chromosome.

"Post-translational modification" as used herein includes glycosylation, but may also involve proteolysis, phosphorylation, acylation, sulfation, γ-carboxylation or β-hydroxylation.

Included within the scope of the present invention is a TC-CSF expressed in a cell including: TC-CSF having the glycosylation and amino acid sequence of a naturally-occurring TC-CSF; human TC-CSF and TC-CSF polypeptides of other animal species, such as bovine TC-CSF, equine TC-CSF, porcine TC-CSF, ovine TC-CSF, canine TC-CSF, murine TC-CSF, and feline TC-CSF, without limitation thereto; deglycosylated or nonglycosylated forms of TC-CSF polypeptides; and analogs of TC-CSF, particularly immunologically and biologically active analogs of TC-CSF.

"Analogs of TC-CSF" include, for example, deletions from, or insertions of or substitutions of, residues within an amino acid sequence of a TC-CSF polypeptide retaining at least 18 consecutive nucleotides in the nucleotide sequence or 6 consecutive amino acids in the amino acid sequence of TC-CSF and retaining a biological or immunological activity of TC-CSF and an overall amino acid and nucleotide sequence homology of at least 80% with a TC-CSF. Combinations of deletion, insertion and substitution may also be made to arrive at a final construct, provided that the final construct possesses an activity of TC-CSF. An "activity" of TC-CSF may be an immunological cross-reactivity with naturally-occurring TC-CSF or may be a biological activity (e.g., a colony stimulating activity) of TC-CSF. It is preferred that mutations made in DNA encoding TC-CSF do not place the sequence out of reading frame and it is further preferred that they do not create complementary regions that produce secondary mRNA structure. Analogs also include polypeptides exhibiting a post-translational modification with which they do not occur in a nature.

Analogs include amino-terminal and carboxyl-terminal fusion peptides of from one residue to polypeptides of any length wherein the analog possesses an activity of TC-CSF, as well insertions of one more amino acid residues within the polypeptide. Such insertions may be of any length which does not prevent the analog from possessing an activity of TC-CSF but are preferably one amino acid in length.

A natural sequence TC-CSF or analogs of a TC-CSF and variants of a TC-CSF may be prepared by direct chemical synthesis of a polypeptide or by expression of DNA prepared by site-directed mutagenesis of TC-CSF DNA or by chemical synthesis of oligonucleotides and assembly of the oligonucleotides by any of a number of techniques prior to expression in a host cell. [See, e.g., Caruthers, U.S. Pat. No. 4,500,707; Balland et al., *Biochimie,* 67 725–736 (1985); Edge et al., *Nature,* 292, 756–762 (1981)]. Messenger RNA encoding TC-CSF or an analog thereof may also be expressed in vitro. Changes in activation levels are measured by an appropriate assay, such as an assay described below. Modifications of such protein properties as redox or thermal stability, hydrophobicity, susceptibility to proteolytic degradation, or the tendency to aggregate with carriers or into multimers are assayed by methods well known to those of ordinary skill in the art.

Prokaryotic microorganisms (such as bacteria) and eukaryotic microorganisms (such as yeast, CHO cells or insect cells) may be employed as host cells according to the present invention. *S. cerevisiae,* or common baker's yeast, is the most commonly used among eukaryotic microorganisms, although a number of other strains are commonly available. For expression in bacteria and yeast, cloning and expression vectors are well known to those skilled in the art, such as lambda phage and pBR322 in *E. coli* and YRp7 in *S. cerevisiae.*

Cells derived from multicellular eukaryotes may also be used as hosts. Cells from vertebrate or invertebrate eukaryotes may be used, and those skilled in the art know of appropriate expression vectors for use therein, such as SV40 vectors for mammalian host cells (such as CHO cells), NPV vectors (such as baculovirus vectors) for invertebrate host cells and Ti vectors for plant cells.

The compositions according to the present invention are formulated in accordance with standard procedures to be adapted for parenteral administration to humans according to techniques known by those skilled in the art.

Typically, the compositions for intravenous administration are solutions of the sterile TC-CSF in sterile isotonic aqueous buffer. Where necessary, the composition also includes a solubilizing agent, or stabilizing or carrier agent. In general, the composition is supplied in unit dosage form, for example, as a dry powder or water-free concentrate in a sealed container such as an ampule. For administration by infusion, the composition may be dispensed from an infusion bottle containing sterile pharmaceutical grade water for injection. For administration by injection, the composition may be dispensed from a vial of sterile water for injection. The injectable or infusible composition may be made up by mixing the ingredients prior to administration.

The effective amount of TC-CSF administered will depend on many factors, including the amount of TC-CSF required and the speed with which it is required.

More specific descriptions of methods, materials, and products according to the present invention appear in the following Examples.

EXAMPLE 1

Process for Isolation of TC-CSF

A TC-CSF may be prepared by stimulation of a murine T lymphocyte cell line, the EL-4 cell line (available as Culture No. ATCC TIB 181 from the American Type Culture Collection, Rockville, Md.) with phorbol 12-myristate 13-acetate (PMA) (Sigma Chemical Company, St. Louis, Mo.). The cells may be grown in RPMI-1640 (GIBCO, Grand Island, N.Y.) containing 5% bovine serum albumin or 5% fetal calf serum at 37° C. in an atmosphere of 5% $CO_2$ in air. For stimulation with PMA, the EL-4 cells may be centrifuged at 500 g for 10 minutes and then resuspended in RPMI-1640, 1% fetal calf serum (FCS) (GIBCO), and 56 units/ml penicillin (GIBCO) 56 $\mu$g/ml streptomycin and 10 $\mu$g/ml glutamine. The cell concentration is then adjusted to $1 \times 10^6$ cells per ml. The volume of the cell suspension may be measured and to this volume a calculated amount of PMA may be added to give a final concentration of 10 ng/ml PMA. The stimulation is preferably done in sterile glass containers with approximately 150 ml of cell suspension in each 500 ml capacity glass container. The cell suspension may be incubated at 37° C. for 2 days in an atmosphere of 5% $Co_2$ in air. Following the incubation the cells may be removed by centrifugation at 2000 rpm for 10 minutes and the supernatant containing the growth factor may be stored at 4° C.

Any residual PMA in the supernatant may be removed by treatment with activated dextran by the following method. For each 100 ml of supernatant 0.3 g Norit A alkaline (Fisher, Pittsburgh, Pa.) and 1.2 g Dextran T 10 (Pharmacia, Piscataway, N.J.) may be suspended in 200 ml phosphate buffered saline (PBS) plus 1% fetal calf serum or in 200 ml RPMI-1640 and 1% FCS. The Norit A and Dextran may be mixed in half the PBS, then poured into 200 ml capacity centrifuge bottles and centrifuged at 2000 rpm for 5 minutes. The supernatant is discarded and the remaining PBS is added to the Norit A and Dextran, the procedure is repeated and the supernatant discarded. Then following these two washes with Norit A and Dextran the growth factor containing culture supernatant may be added to the Norit A plus Dextran, mixed and centrifuged at 2000 rpm for 5 minutes. The growth factor conditioned medium supernatant is poured off and then may be filtered through a $0.45\mu$ filter as available from Millipore Corporation, Bedford, Mass.

EXAMPLE 2

Bioassay for TC-CSF

The hematopoietic growth stimulating activity of a conditioned medium may be tested utilizing the agar clonal assay. Following stimulation with a growth factor, hematopoietic progenitor cells form colonies in the agar cultures. Hematopoietic cells utilized for the bioassay may be derived from bone marrow or spleen of rodents such as C57B1/6J mice.

Following euthanasia of a mouse, the femur is dissected out and bone marrow cells may be flushed out with RPMI-1640 using a syringe and needle. The cells may be dispersed by pipetting, and a single cell suspension may be derived. The viable cell count maybe obtained by Trypan blue exclusion of cells counted in a hemocytometer. Bone marrow cells may be plated at $1 \times 10^5$ or $5 \times 10^4$ cells per plate. Duplicate or triplicate plates may be set up. The cell cultures may be set up in 0.3% agar (Bactoagar, GIBCO) in Dulbecco's medium (GIBCO) with 20% horse serum (GIBCO), supplemented with 56 units/ml penicillin and 56 $\mu$g/ml streptomycin. TC-CSF-conditioned media maybe added at 10% V/V to the agar cultures. The cultures are then incubated at 37° C. for seven days in an atmosphere of 10% $CO_2$ in air.

EXAMPLE 3

Bioactivity of TC-CSF

The colonies formed following stimulation with conditioned media containing TC-CSF may be enumerated microscopically at 40× magnification. Colony Forming Unit-culture (CFU-C) colonies contained 50 or more cells.

The lineage specificity of CFU-C colonies may be determined by morphological assessment of the cells comprising each colony. Intact agar cultures may be dehydrated on glass slides and stained for acetylcholinesterase. A counterstain that may be utilized for nuclei is methyl green. The colonies may then be examined microscopically, the nuclear configuration, cell shape and size allow differentiation between the cell lineages such as granulocytic, mononuclear, fibrocytic stromal and megakaryocytic. In addition, the megakaryocyte cytoplasm stains brown due to the presence of acetyl cholinesterase. Clusters of three or more megakaryocytes may be taken as representing a megakaryocyte colony.

TC-CSF-containing conditioned media, as prepared in procedure of Example 1, stimulate the formation of approximately 90±20 CFU-C colonies (mean±2 SD) and 20±4 CFU-M (megakaryocyte colonies), per $1 \times 10^5$ bone marrow cells. Morphological analysis of the colonies reveals that TC-CSF-generated colonies are composed of: granulocytes; macrophages; megakaryocytes; mixtures of granulocytes and macrophages; mixed colonies which were very large compared with the other colonies, (mixed colonies consist of more than 150 cells entities composed of granulocytes, macrophages and megakaryocytes); and fibrocytic stromal cell colonies.

EXAMPLE 4

Isolation of TC-CSF

Protein fractions, contained in the conditioned media derived as in the final product of Example 1, may be separated by high pressure liquid chromatography (HPLC) on an anion-exchange column DEAE-5PW, 7.5 mm×7.5 cm, available from Waters Associates, Milford, Mass. A phosphate buffered saline gradient may be utilized for elution with a gradient range from 10 mM NaCl to 1 M NaCl. The fractions may be collected at a flow rate of 0.5 ml/min and then each fraction may be assayed for colony stimulating activity as described in Examples 2 and 3. Bioassay for colony stimulating activity of the fractions demonstrated peak activity with a 0.23 M NaCl gradient. There may be more than a 90% recovery of activity compared to the initial conditioned medium. The activity of the TC-CSF at 0.23 M NaCl gradient serves to distinguish the TC-CSF molecule from interleukin-3 (IL-3), which may also stimulate hematopoietic colony formation, because IL-3 does not bind to DEAE and runs through a DEAE column before the NaCl gradient fractions.

The TC-CSF molecule may be separated from other molecules based upon the size of the TC-CSF molecule obtained by gel filtration. A molecular sieve column protein Pak 125 (size cut-off for native globular protein, 2,000 to 80,000 daltons), 7.8 mm×30 cm, from Waters Associates may be utilized with HPLC at a flow rate of 0.5 ml/min. A variable wavelength spectrophotometer and an integrator/recorder may be attached to the detector set at 280 nm to record and integrate the chromatograms. The fractions may be collected in PBS (pH 7.3), and then each fraction assayed for colony stimulating factors. Assays of the fractions indicated activity was present in three fractions, and corresponding peaks of optical density at 280 nm indicated the presence of protein in the active fractions. A first fraction corresponds to a molecular mass (MW) of 65 to 70 kilodaltons (Kd), consistent with the trace amount of bovine serum albumin and bovine fetal albumin present in the conditioned media. A second fraction may have peak activity and corresponds to MW 50 to 55 Kd. A third fraction with minimal activity corresponds to MW 25 to 30 Kd.

EXAMPLE 5

Molecular Weight Assessed by Electrophoretic Mobility

The bioactive second fraction derived after HPLC gel filtration in Example 4 and the unseparated conditioned media may be further analyzed by polyacrylamide gel electrophoresis (PAGE). Either polyacrylamide urea gel electrophoresis at pH 9.9 in a reducing buffer of 50 mM 2-mercaptoethanol (2-ME) and 10 M urea, or SDS-PAGE in 0.3% SDS, 7.5% acrylamide and 10 mM 2-ME in glycerol buffer my be employed. Samples may be run 50 $\mu$l per lane with growth factor media or molecular weight markers purchased from Pharmacia. Lanes run with molecular weight markers and designated samples respectively, may be stained by silver stain to identify the protein molecule according to electrophoretic mobility. The TC-CSF demonstrates an electrophoretic mobility in PAGE under reducing conditions corresponding to a MW of about 55 Kd.

Confirmation of bioactivity in the molecule identified by electrophoretic mobility may be obtained by running lanes containing the sample under investigation. Following electrophoresis the entire lane may be sectioned into 1 mm wide slices starting from the cathodal end and proceeding towards the anodal end. The protein from each 1 mm slice may be eluted in 1 ml PBS at pH 7.2 and then assayed for colony stimulating factor. Adjacent lanes with appropriate molecular weight markers may be stained to determine the electrophoretic mobility of the bioactive molecule, which corresponded to a MW of about 55 Kd.

Following bioassay of the protein derived from the gel slice, a portion of the eluate may be re-run on SDS-page and following stain with silver stain demonstrate a single protein band at about 55 Kd. Thus confirmation may be derived that bioactive TC-CSF molecule has a MW of about 55 Kd, demonstrated by electrophoretic mobility under reducing conditions.

EXAMPLE 6

Protein Content and Potency of TC-CSF

The protein content of the TC-CSF containing media and that of the fractions may be measured by microassay procedure. Spectrophotometric analysis is possible at 595 nm following reaction with protein assay dye reagent available from Bio-Rad, Richmond, Calif., and the protein content may be determined from a standard curve prepared with BSA.

After the least measurable protein content has been estimated, further dilutions may be made and the protein content calculated. Assays of dilutions of the fractions correlated with 10 to 14 nanograms of protein stimulate 5 to 8 CFU-C per $1 \times 10^5$ bone marrow cells. This corresponded to activity at a 1 to 2 picomolar concentration of TC-CSF, an indication of the potency of the growth factor.

EXAMPLE 7

Production of an Antibody Against a TC-CSF and Assays

Animals such as Balb/c mice or Lewis rats may be immunized by intraperitoneal injection of a TC-CSF-containing fraction obtained following HPLC column separation as in Example 4. The growth factor-containing fraction may be combined with Freund's adjuvant (one part in three) and injected into the animals, followed by a booster dose 4 weeks later, after which the animals may be sacrificed and the sera obtained.

In an ELISA assay, the second HPLC-derived fraction from Example 4 containing the TC-CSF may be used as antigen, and diluted in coating buffer to give a final protein concentration of about 0.5 µg/ml (coating buffer is prepared by dissolving 0.795 g anhydrous $Na_2CO_3$ and 1.466 g $NaHCO_3$ in 450 ml of deionized water at pH 9.6). Next, 100 µl of the diluted antigen may be added to each well of micro ELISA plate (Corning) and then the plates may be placed in a covered container at 4° C. overnight. The plates may then be removed and each well washed 3 times with 200 µl of PBS/Tween-20™ (stock solution prepared by adding 1.5 ml Tween-20™ to 1000 ml PBS). The antibody containing sera is added 1:50 in PBS/Tween-20™ and 100 µl of the diluted antiserum may be added to the wells and incubated for one hour at 37° C. The wells may then be washed three times and 100 µl of anti-mouse IgG alkaline phosphatase conjugate (Sigma) which had been diluted 1:1000 in stock PBS/Tween-20™ may be added to each well. Following a further one hour incubation at 37° C., the wells may be washed three times and 100 µl volume of diethanolamine substrate (Sigma) may be placed in each well. A positive reaction is observed by yellow color formation within a half hour, indicating specific reaction with TC-CSF (antigen) and antibody contained in the sera. Following addition of the antibody sera in dilutions of 1:1000, about 56% of the colony stimulating activity of the TC-CSF fraction is neutralized.

Sera from immunized, antibody-producing animals tested positive when screened against TC-CSF-containing fraction by the ELISA technique using reagents obtained from Sigma Chemical Company. Control sera from uninjected mice and those injected with Freund's adjuvant alone tested negative. The antibody may be tested for neutralizing activity in the bioassay with the TC-CSF containing growth factor providing colony stimulating activity.

In a Western blot analysis, the HPLC gel filtered TC-CSF of the second fraction of Example 4 may be run on SDS-PAGE electrophoresis and then may be placed in the transblot system (Hoeffer Scientific, San Francisco, Calif). The protein bands may then be transferred onto nitrocellulose sheet which may then be incubated for one hour in blocking buffer (Sigma). Antibody may then be added and a further one hour incubation done. Following three washes antimouse IgG alkaline phosphatase conjugate (Sigma) may be added, and, following an hour incubation and five washes in PBS/Tween-20™, the substrate Naphthol As-Mx phosphate sodium salt (Sigma) may be added. A positive reaction is determined by Immunostain with Fast red substrate (Sigma). The protein bands in adjacent lanes may be visualized by staining for protein such as with Amido Black.

Thus, the specificity of the antibody against the TC-CSF is also observed in a Western blot analysis. The antibody strongly react with the protein band at 55 Kd. Reaction was also seen with bands at 67 Kd and 65 Kd which corresponded to fetal calf albumin and bovine serum albumin respectively, the albumin being a carrier protein for the growth factor molecules. No reaction is seen with proteins below 55 Kd MW.

The antibody sera may be tested against IL-3 to look for cross-reactivity. No neutralization of IL-3 activity is observed. This serves to distinguish TC-CSF from IL-3.

Antibody against a TC-CSF may be purified from sera using techniques well known to those skilled in the art and including passing TC-CSF antibody-containing fluid over a column to which is bound TC-CSF, such as material derived from the active second fraction of Example 4. Similarly, TC-CSF may be purified by a procedure including a step of passing a fluid containing TC-CSF over a column to which anti-TC-CSF antibody is bound.

EXAMPLE 8

Effect of Other Antibodies On TC-CSF

Specific antibodies against several growth factors implicated in hematopoiesis may be tested against the TC-CSF growth factor to assess for any neutralization, using the agar clonal assay as described in Example 2 and 3. Some of these antibodies are directed against IL-3, GM-CSF, BSF-1 and the IL-2 receptor. Monoclonal antibodies may be tested in a 1:1 dilution with the TC-CSF growth factor fraction and animal sera containing antibody in a dilution of 1:500. The specificity of the antibodies and thus their ability to neutralize the respective growth factors or receptor has been established previously. [See, for example anti-IL-2 receptors antibodies 3C7 and 7D4, Ortega et al., *J. Immunol., 133,* 1970 (1984); Malek et al., *J. Immunol., 133,* 1976 (1984); anti-murine recombinant GM-CSF, Mochizuki et al., *J. Immunol., 136,* 3706 (1986); for anti-IL-3, monoclonal antibody 19B3.1, Abrams et al., *J. Immunol., 140,* 131 (1988); anti-BSF-1, monoclonal antibody 11B11, Ohara et al., *Nature, 315,* 333 (1985).] No neutralizing activity by these antibodies on the TC-CSF is observed. This result illustrates that the TC-CSF is distinct from these other growth factors.

EXAMPLE 9

Amino Acid Composition of TC-CSF

The amino acid composition of a TC-CSF sample may be prepared in the following manner. Following gel electrophoresis as in Example 5, a TC-CSF-containing gel may be blotted on to a PVDF blot membrane at 90 volts for 24 minutes. The TC-CSF protein band may be identified by staining with Coomassie blue and the band excised and used in a Waters Pico Tag amino acid analysis system. The method involves hydrolysis and precolumn derivatization of the sample followed by reverse phase HPLC. It is based on the application of the phenylisothiocyanate (PITC) chemistry developed by Edman for amino terminal residue sequencing of proteins using PITC as a tagging reagent in the precolumn derivatization of protein and peptide hydrolysates. The following protocol may be employed: 1) collect and dry the samples; 2) hydrolysis at 110° C. for 24 hours; 3) dry the sample further; 4) derivatization; 5) liquid chromatography and 6) data analysis.

An example of the data derived is given in Table 1. It should be noted that, in this determination, the percent of sample injection in the final volume is 50%. The amino acids tryptophan and cysteine are destroyed during acid hydrolysis.

TABLE 1

| Amino Acid | Picomoles | Percent | Predicted Number in TC-CSF |
| --- | --- | --- | --- |
| Asx | 81.60 | 7.36 | 41 |
| Glx | 138.52 | 12.49 | 69 |
| Ser | 77.18 | 6.96 | 38 |
| Gly | 121.74 | 10.98 | 60 |
| His | 23.35 | 2.11 | 11 |
| Arg | 40.14 | 3.62 | 20 |
| Thr | 39.14 | 3.53 | 20 |
| Ala | 65.98 | 5.95 | 33 |
| Pro | 42.44 | 3.83 | 21 |
| Tyr | 36.49 | 3.29 | 18 |
| Val | 43.77 | 3.95 | 22 |
| Met | 10.59 | 0.96 | 5 |
| Cystine | 36.31 | 3.27 | 18 |
| Ile | 70.09 | 6.32 | 35 |
| Leu | 32.90 | 2.97 | 16 |
| Phe | 125.43 | 11.31 | 62 |
| Lys | 123.34 | 11.12 | 61 |

The amino acid composition data supports the results reported in other Examples indicating a TC-CSF has a MW of about 55 Kd, and is distinct from other known hematopoietic growth factors.

EXAMPLE 10

Amino Acid Sequencing

An Applied Biosystems sequencer (Applied Biosystems, Foster City, California) automates the determination of amino acid sequences of proteins. A sample may be prepared in the following manner. Following gel electrophoresis as in Example 5, the gel may be blotted on to PVDF blot membrane at 90 volts for 24 minutes. The TC-CSF protein band may be identified by staining with Coomassie blue and the band excised and placed in a column of the sequencer for sequencing following the procedure recommended by the manufacturer. The sequencer controller may then collect and analyze the chromatographic data to interpret the information.

Interpretation of chromatographic data on amino acid sequencing of TC-CSF suggested an amino terminal residue sequence of SEQ ID NO: 3.

EXAMPLE 11

Differentiation of TC-CSF from other Known Hematopoietic Growth Factors

A growth factor TC-CSF according to the present invention has a MW of 55 Kd and multi-lineage activity. As noted above, none of IL-3, GM-CSF, CSF-1, and G-CSF have a MW exceeding about 30 Kd. The activity of this growth factor, is not inhibited by specific antibodies against IL-3, GM-CSF, BSF-1 and anti-IL-2 receptor. Comparison of protein conformation and amino acid distribution has been made with albumin, CSF-1, GM-CSF and IL-3 with no demonstration of homology.

Furthermore a partial sequence of the TC-CSF has been compared with albumin, CSF-1, GM-CSF, G-CSF, IL-3, BSF-1, BSF-2, IL-6 and neuroleukin, with no demonstration of proper homology. Neuroleukin was included because it is a T cell lymphokine which has a MW of 56 Kd, although no hematopoietic growth factor activity has been demonstrated by this molecule.

The partial sequence of TC-CSF was compared against a data base consisting of over 1 million residues in 4749 sequences. Highest scores were obtained with the coat protein of bacteriophage q-be, fibronectin and viral polyprotein. This suggests that TC-CSF may have some similarities with these proteins but is not identical to them. It also serves to distinguish TC-CSF further from other known growth factors which may be implicated in hematopoiesis.

EXAMPLE 12

Construction of TC-CSF Oligonucleotides

Oligonucleotides encoding portions of TC-CSF may be synthesized using the above amino acid sequence by the procedure of Caruthers, U.S. Pat. No. 4,415,732 and deoxyribonucleic acid and ribonucleic acid probes and primers for site-directed mutagenesis (e.g., for use in polymerase chain reaction assay or amplification procedure) may be made by in vitro transcription of the oligonucleotides.

Plasmids including DNA sequences according to the present invention may be labeled with a radioactive isotope or with a non-radioactive chemical tag and used as probes. Such plasmids may also be used to synthesize the labeled RNA probes. The labeled probes may be used to detect the presence of homologous DNA sequences and/or mRNA sequences encoded by these DNA sequences in cells of any species, for example by the Southern or Northern hybridization procedure or by dot blot or slot blot hybridization or by in situ hybridization techniques. Stringent hybridization conditions for hybridization assays according to the present invention may generally be defined as reactions functionally equivalent to hybridization carried out in 4×SSC and 0.5% SDS at a temperature of 65° C. in the last wash.

Nonstringent hybridization conditions, for identifying TC-CSF encoding DNA by screening cell libraries may be determined by principles known to those skilled in the art of cloning homologous genes.

Oligonucleotides according to the present invention may be bound to beads or may be labeled for use in assays by methods well understood by those skilled in the art.

EXAMPLE 13

TC-CSF Peptides and Antibodies Thereto

Peptides corresponding to different portions of TC-CSF proteins, preferably 12–20 amino acid residues in length, may be chemically synthesized by solid-phase methods. Any TC-CSF polypeptides or analogs according to the present invention may be used to elicit specific polyclonal and monoclonal antibodies [Lerner, *Nature*, 299, 592–596 (1982); Niman et al., *Proc. Natl. Acad. Sci. (USA)*, 80, 4949–4953 (1983)]. The amino acid sequence of TC-CSF facilitates the design of immunogenic peptides corresponding to suitable immunogenetic regions which may be determined according to procedures well known to those skilled

EXAMPLE 14

Recombinant Expression of TC-CSF

Complete and partial TC-CSF gene products and analogs may be expressed in bacteria, yeast or mammalian expression systems obtained using products based on amino acid sequences derived from isolated TC-CSF according to the present invention by inserting the DNA encoding TC-CSF into an expression vector, for example a plasmid, phage or viral expression vector [Vieira et al., *Gene*, 19, 259–268 (1982); Young et al., *Proc. Natl. Acad. Sci. (USA)*, 80, 1194–1198 (1983); Bitter et al., *Gene*, 32, 263–274 (1984); Cepko et al., *Cell*, 37, 1053–1062 (1984); and Gorman et al., *Mol. Cell. Biol.*, 2, 1044–1051 (1982)].

The expressed proteins or polypeptides may be purified, for example in Example 4, and used to raise specific antibodies (an epitope comprising about 6 or more amino acids as encoded by 18 or more nucleotides, respectively) or as ligands for antibodies such as may be employed in an immunoassay.

EXAMPLE 15

Probes and Screening for TC-CSF Clone

Oligonucleotide encoding portions of TC-CSF were synthesized using a partial amino acid sequence of TC-CSF set out in SEQ ID NO: 4 which was derived from resequencing of TC-CSF and interpretation of the results thereof.

The CDNA library was constructed from murine T lymphocytes, the EL4 cell line, in the Lambda Zap 11™ vector that contained the Bluescript™ plasmid [Bullock et al., *Biotechniques*, 5, 376–379 (1987)]. The cDNA library was acquired from the commercial vendor of this product (Mouse EL4 cDNA Library, Product No. 936303, Stratagene Cloning Systems, La Jolla, Calif.). The primer for the library was oligo-(dT), average insert size 1.0 Kb and cloning site EcoRI. The number of primary plaques was $2.0 \times 10^6$ with an estimated titer of $4.0 \times 10^9$/ml. The host strain recommended for screening and amplification in the Stratagene product literature was XL1-Blue™.

By the procedure of Caruthers U.S. Pat. No. 4,415,732, a 17-mer probe was constructed with 64 permutations. The TC-CSF oligonucleotides were labeled with radioactive phosphorous ($^{32}$p) and used as probes to screen the CDNA library derived from EL4 cells in the lambda bacteriophage vector. In order to establish specificity of the oligonucleotides for cDNA in the library, unlabeled oligonucleotides were used as primers in the polymerase chain reaction and for in vitro transcription from the primer. The target DNA was $8.1 \times 10^8$ lambda bacteriophage clones containing cDNA from the EL4 cell line. The primers for the PCR were (i) the oligonucleotide and (ii) either the T3 or T7 RNA Polymerase promoter for the lambda bacteriophage. The deoxyribonucleotide triphosphates (dNTPs) were used at saturating conditions (200 micromolar for each DNTP) and Taq DNA Polymerase (Perkin Elmer Cetus N801-0046) at approximately 2 units to catalyze a typical amplification reaction. The cycle profile for an amplification reaction may be: denaturation at 94° C. for 1 minute; annealing at 50° C. for 1 minute; and polymerization 72° C. for 2 minutes for 30 cycles and then the difference in the last cycle may be Polymerization at 72° C. extended for 5 minutes. An aliquot (10 μl) of the reaction mixture was subjected to 1% agarose gel electrophoresis and revealed a major amplification product of approximately 800 base pair size. This established that the oligonucleotides were specific for target DNA contained in $8.0 \times 10^8$ lambda bacteriophage clones containing cDNA from EL4 cells. The next step was to screen smaller library aliquots in order to identify the clone.

An initial PCR filter screening was done. A total of six filters were prepared each containing $1 \times 10^6$ plaque forming units. Preparations from each of these filters were amplified using the oligonucleotides constructed from the amino acid sequence of TC-CSF as above. A major PCR product of approximately 800 base pair size was seen and a number of discreet products ranging from approximately 250 to 1000 base pairs were observed. Therefore, the PCR products were evaluated by Southern hybridization. The amplified material from the filters was electrophoresed on a 1.2% agarose gel and capillary blotted onto a nylon membrane. The blotted DNA was hybridized with radiolabeled oligonucleotides. Even under stringent hybridization conditions the 800 base pair major band hybridized to the labeled oligonucleotides. The conditions being equivalent to hybridization carried out at 4×SSC and 0.5% SDS at a temperature of 65° C. in the last wash. This indicated that the oligonucleotides were specifically hybridizing to DNA contained in the $1 \times 10^6$ plaque on the filter.

Next, plaque hybridization was done. A total of 10 filters each containing immobilized protein from $5 \times 10^4$ Pfu were hybridized with the $^{32}$p labeled oligonucleotide. Successful hybridization was established by autoradiography. Under conditions of lower stringency, six putative positive clones were identified. Under conditions of high stringency, one clone was strongly positive. The Pfu on the probe corresponding to the immobilized positive clone on the filter was picked and expanded in *E. coli* XL1-Blue cells.

The Lambda Zap 11™ vector (stratagene) allows the in vivo subcloning of the cloned insert contained in the Bluescript™ plasmid within the lambda vector to form a phagemid containing the cloned insert. The methodology was as per Stratagene technical manuals and product literature. The R408™ helper phage and XLI-Blue cells (Stratagene) were used to successfully excise the cloned DNA insert. The nascent insert containing phagemid was secreted from the *E. coli* through pilii by signals contained within the f1 terminator origin DNA sequence. Following secretion of the phagemid that was resistant to the heat treatment the *E. coli* cells were removed from the supernatant by heating at 70° C. Miniprep DNA was made by transfection of the fresh *E. coli*. The DNA derived from preparations of these colonies was used for analysis and sequencing of the insert.

The insert contained between the T3 and T7 RNA polymerase promoters was rescued and analyzed on 1% agarose gel. The size of the insert was approximately 2.3 Kb. All appropriate controls and markers were used for the analysis. A good yield of cloned DNA was obtained with the helper phage R408™ (Stratagene) and used for dideoxynucleotide sequencing. Following lysis with alkali, recovery and purification were either by fractionation in low-melting-temperature agarose gels or by equilibrium centrifugation in cesium chloride-ethidium bromide gradients. The DNA was labeled using [$S^{35}$]-DATP labeling mixture and cut with the restriction enzyme EcoRI for sequencing.

EXAMPLE 16

Sequencing of TC-CSF Clone

The method used for DNA sequencing was the enzymatic method of Sanger et al., *Proc. Natl. Acad. Sci.*, 74, 5463

(1977). Taq DNA polymerase, AmpliTaq™ (Perkin Elmer Cetus) was used for the chain extension and chain termination reaction mixtures, together with solutions of dNTPs and ddNTPs. Denaturing polyacrylamide sequencing gels were run and read after autoradiography of the sequencing gels. Uniform band intensities were observed in the sequencing ladders for 257 nucleotide sequences at the 5' end and 234 nucleotide sequences at the 3' end. The nucleotide sequence with the corresponding amino acid sequence for murine TC-CSF is given in SEQ ID NO: 1. Verification and confirmation of the specificity of the sequence for murine TC-CSF was done by isolating and sequencing a few other clones that were weakly positive with the oligonucleotide probe under less stringent conditions and some negative clones. No homology was identified with the sequence of these other clones with that of the sequence of the oligonucleotide probe.

The sequence of murine TC-CSF was compared with sequences of other known growth factor molecules and no real homology was demonstrated with other growth factor molecules. Only four amino acids in sequence in TC-CSF matched four amino acids in murine IL-3. These were Lys-Ser-Asn-Leu in position 71–74 in TC-CSF and in position 97–101 in IL-3. However the nucleotide sequence for these four amino acids in the two molecules was entirely different.

It is believed that SEQ ID NO: 1 is a nucleotide sequence from a partial clone in that the first 11 nucleotides are part of a restriction site. Accordingly, in SEQ ID NO:2, an amino acid sequence is presented which is deduced from the nucleotide sequence of SEQ ID NO: 1 supplemented by Pro-Leu as second and third residues (as obtained from prior nucleotide sequencing in a T7 vector) and an initial Met (as obtained in amino acid sequencing). Stop codons prior to position 1662 of SEQ ID NO:1 have been identified as unknown residues (i.e., "Xaa") in SEQ ID NO: 2 on the basis that amino acid composition data indicate that the length of mouse TC-CSF is approximately 554 amino acids, and that, therefore, stop codons prior to position 1662 represent mutations or sequencing errors. One skilled in the art may amend SEQ ID NO: 2 upon consideration of the repeated amino acid sequence data of the following example.

EXAMPLE 17

Repeated Amino Acid Sequencing

Repeat amino acid sequencing resulted in the identification of 45 amino acids from the amino terminal end as disclosed in Table 2.

TABLE 2

| | |
|---|---|
| 1. Met | 24. Leu |
| 2. Pro | 25. Tyr or Pro |
| 3. Leu or Glu | 26. Phe |
| 4. Leu | 27. Cys or Ser |
| 5. Cys or Gly or Tyr | 28. Pro or Ile |
| 6. Ala | 29. Ile |
| 7. Ser | 30. Leu or Phe or Tyr |
| 8. Gly or Glu | 31. Ser or Tyr |
| 9. Asp | 32. Ser or Phe or Ile |
| 10. Thr | 33. Ile |
| 11. Pro | 34. Tyr or Ser |
| 12. Met | 35. Phe |
| 13. Pro | 36. Ser |
| 14. Glu | 37. Ile |
| 15. Asn or Lys | 38. Ser |
| 16. Leu | 39. Ser or Ile |

TABLE 2-continued

| | |
|---|---|
| 17. Asp or Glu | 40. Ile |
| 18. Tyr | 41. Phe |
| 19. Thr | 42. Ser |
| 20. Phe | 43. Tyr |
| 21. Tyr | 44. Gly or Tyr or Lys |
| 22. Glu or Ser | 45. Lys |
| 23. Glu | |

Comparison of the nucleotide sequence with amino acids 1–45 from the amino terminus reveals that there is an initial Met before the Pro.

Amino acid no. 12 encodes a Met, with the nucleotide sequence being GTG. This may code either for Met or Val.

Amino acid no. 42 is serine; the nucleotide sequence is TAA, an ochre mutation.

Amino acid no. 43 is Tyr; the nucleotide sequence is TAG, an amber mutation.

EXAMPLE 18

Anti-Idiotypic Antibodies to TC-CSF

Anti-idiotypic antibodies may be made from antibodies raised against any species TC-CSF, as for antibodies to mouse TC-CSF described above. See, e.g., Kennedy et al., *Scientific American*, 48–56 (July 1986); Jerne, *Scientific American*, 52–60 (July 1973); Marx, *Science*, 228, 162–165 (1985); Finberg et al., *CRC Critical Reviews in Immunology*, 7, 269–284 (1987); and Kennedy et al., *Science*, 232, 220–223 (1986).

EXAMPLE 19

Screening for the Human TC-CSF Clone

Expressing the cloned human gene obtained by using the amino acid, nucleotide sequences or antibodies disclosed herein, permits the use of TC-CSF by patients with an otherwise fatal disease. Steps for cloning the human gene are described as follows. Partial homology was established between the cloned murine gene and genomic DNA from a human Jurkat T lymphocyte cell line by Southern hybridization. A cDNA library was constructed from the Jurkat human T lymphocyte cell line in a lambda bacteriophage vector. Labeled probes based on the murine gene were utilized to screen the library.

Although the murine gene was used as a probe, fragments of the gene or oligonucleotides synthesized from the murine gene sequence may be used as probes or as primers in a polymerase chain reaction with target DNA derived from human T lymphocytes. The amplification products may be labeled and used as probes to screen the library or sequenced to detect the presence of homologous DNA sequences between species. Based upon these sequences oligonucleotide probes may be synthesized to screen the human library.

Specifically the cloned insert containing the gene for murine TC-CSF was labeled with $^{32}p$ and used as probe to screen the human T cell library for the human TC-CSF gene.

The cDNA library was constructed from human T lymphocytes, the Jurkat cell line, in the Lambda Zap 11™ vector that contained the Bluescript™ plasmid. The cDNA library was acquired from the commercial vendor of this product (human Jurkat cDNA Library, Product No. 936204, Stratagene Cloning Systems, La Jolla, Calif.). The primer for the library was oligo-(dT), average insert size 0.8 kb. The cloning site restriction enzyme digestion was EcoRI. The number of primary plaques was 2.0×10⁶, with an estimated titer of 2.0×10¹⁰/ml. The host strain recommended for screening and amplification was XL1-Blue™ E. coli.

Plaque hybridization was done with a total of 30 filters, each containing immobilized protein from 5×10⁴ plaque forming units. Successful hybridization was established by autoradiography. Even under low stringency conditions only one positive clone was identified. Following confirmation at higher stringency the clone was picked and expanded. The in vivo subcloning, excision and rescue o f the insert was done as per Stratagene technical manual as described in Example 15 for the murine gene.

The size of insert w as approximately 800 bases. Miniprep DNA was made following alkali lysis; recovery and purification either by fractionation in low-melting-temperature agarose gels or by equilibrium centrifugation in cesium chloride-ethidium bromide gradients. The DNA was labeled with S³⁵dATP labeling mixture and cut with restriction enzyme EcoRI for dideoxynucleotide sequencing.

The cDNA for TC-CSF was cloned in the helper phage M13 and sequenced by the Sanger method as described previously. The entire nucleotide sequence for cDNA of TC-CSF has been analyzed and potential initiation codons have been identified. From the nucleotide sequence and the encoded amino acid sequence, it is apparent that the entire gene has been cloned and that the TC-CSF is a monocistronic product.

EXAMPLE 20

Sequencing of the Human TC-CSF Clone and Homology with Murine TC-CSF Clone.

The method used for DNA sequencing was the enzymatic method of Sanger et al., as described in Example 16. The nucleotide sequence and a deduced amino acid sequence for human TC-CSF is given in SEQ ID NO: 5, stop codons (as indicated by an asterisk, "*", in SEQ ID NO: 5) may result from sequencing errors, contamination or sequencing of complementary DNA formed from mRNA as described below. A preliminary expression product of about 110 amino acids in length may correspond to the open reading frame between position, 133 and 540. FIG. 2 is a depiction of the reverse complement of the coding region.

Homology with the murine TC-CSF was determined and is given in Table 3 wherein amino acids which are identical in both mouse and human TC-CSF are indicated by an asterisk above the human sequence.

TABLE 3

Sequence comparison of Human and Murine Homologous Regions

|  |  |  |   | * |   | * | * |   | * |  |
|---|---|---|---|---|---|---|---|---|---|---|
|  |  |  | W | Y | W | T | F | V | I | K |
| Human | 81 | T | TGG | TAC | TGG | ACC | TTT | GTA | ATT | AAA | 105 |

|  |  |  | Y |   |  | F | V | R | K |  |
|---|---|---|---|---|---|---|---|---|---|---|
| Murine | 840 |  | CC | TAC |  | 845 TTT | GTG | CGA | AAG | 856 |

|  |  |  |  | * |  |  | * | * |  |
|---|---|---|---|---|---|---|---|---|---|
|  |  | I | N | L | F | Y | N | S | N |
| Human | 106 | ATT | AAT | TTA | TTT | TAC | AAT | AGT | AAC | 129 |

|  |  | G | S | L |  | N | S | S |  |
|---|---|---|---|---|---|---|---|---|---|
| Murine | 857 | GGT | TCC | TTA | 869–1076 AAT | AGT | TCA | 1084 |

TABLE 3-continued

Sequence comparison of Human and Murine Homologous Regions

|  |  |  | * | * |  | * | * | * |  |  |
|---|---|---|---|---|---|---|---|---|---|---|
|  |  | S | P | V | W | K | K | K | Q |  |
| Human | 130 | TCA | CCT | GTA | TGG | AAA | AAA | AAA | CAA | 153 |

|  |  |  | P | V |  | K | K | K | S |  |
|---|---|---|---|---|---|---|---|---|---|---|
| Murine | 1094 |  | CCT | GTT | – – | AAA | AAA | AAA | TCA | 1117 |

|  |  | * |  |  | * |  | * | * |  |
|---|---|---|---|---|---|---|---|---|---|
|  |  | P | A | L | F | G | A | L | D |
| Human | 154 | CCA | GCT | CTG | TTT | GGT | GCT | TTG | GAT | 177 |

|  |  | P |  |  | F | E | T | L | D |  |
|---|---|---|---|---|---|---|---|---|---|---|
| Murine | 1118 | CCC | – – | – – | TTT | GAG | ACT | TTG–GAT | 1150 |

In Table 3 the human sequence for TC-CSF has been matched for homology with the murine TC-CSF sequence. The homologous region in the human sequence was 100 bases extending from nucleotide sequence No. 81 to 177 (nucleotide and amino acid sequence, SEQ ID NO:9; amino acid sequence, SEQ ID NO:10). In the murine sequence (nucleotide and amino acid sequence, SEQ ID NO: 11: amino acid sequence, SEQ ID NO: 12) the region spanned 310 bases from nucleotide sequence No. 840 to 1150. Within this region of 310 bases in the murine sequence there was a break in homology of 210 bases from nucleotide sequence No. 865 to 1076. Between murine sequence No. 1100 to 1105 there was a break of two amino acids denoted by two bars (these were T and E), compared with one amino acid in the human sequence. Between sequence No. 1121 to 1132 there was a break of four amino acids denoted by four bars (these were F; T; V; S [SEQ ID NO:13]), compared with two amino acids in the human sequence. Homologous amino acids were indicated by an asterisk above the human sequence. Each homologous region constituted approximately 15% of the DNA sequence in the respective gene inserts.

Homology between the sequence of the human gene and murine gene was seen concentrated over some regions in the two gene inserts. This homologous region was between nucleotide sequences 81 to 180 in the human DNA sequence and between nucleotides 840 to 1150 in the murine DNA sequence. The 100 nucleotides contained in this region in the human gene and the 310 nucleotides contained in the region demonstrating homology in the murine gene, constitute approximately 15% of each DNA sequence in the respective gene inserts. The larger span in the murine sequence that is homologous to the human DNA sequence may be considered to be due to, regions of intervening sequences that are usually untranscribed in mRNA and present in the murine DNA sequence and in nuclear RNA.

Hematopoietic growth factors such as GM-CSF and IL-3 are known to have two different mRNAs with striking structural similarities. Splicing of the heterogeneous nuclear RNA (hnRNA) results in mRNA of various lengths. The precursor hnRNA encodes the same protein as the short mRNA, however it is longer due to the additional peptides at the amino terminus domain, encoded by the additional sequences at the 5' region. The hnRNA may have more than one AUG initiation codon, however, translation in vitro has been demonstrated to initiate at the first AUG in preference to the second or third. Furthermore, it is known that in 95% of eukaryotic mRNAs translation begins at the AUG codon closest to the 5' end of the mRNA (Kozak, *Nucleic Acid Res.*, 12, 857 (1984)). In DNA libraries made from RNA containing hnRNA the sequence may include intervening sequences that are not included in cDNA libraries made from mRNA.

It may be considered that the murine TC-CSF formed in vitro by PMA stimulation of the EL-4 cells, may contain TC-CSF synthesized from hnRNA that has the additional 5' residues. Oligonucleotide probes constructed from the amino acid sequence of the amino terminus domain of the protein may select for the hnRNA derived DNA clone. Restriction enzyme digestion by EcoRI of the plasmid containing the murine clone yielded a single fragment only that was 2.6 kb long, consistent with this being a single insertion at the cloning site.

The labeled murine insert that was used to screen the human library may select the clone in which transcribed homologous regions were present. Thus preferentially selecting the homologous mRNA-derived cDNA clone from the human library. This explained the smaller insert size of 800 bases of the human clone with the "concertina like" effect on the homologous region compared with the murine DNA sequence. Further evidence that the transcription region for mRNA in the murine gene may be approximately 800 bases was evident from the in vitro transcription product of 800 bases in the PCR described in Example 14. Polymerase chain reactions with an anchored primer for sequences at the 5' region of the murine gene, with second primers each from sequences at varying distance from the 3' end, including vector sequences flanking the insertion site, in reactions with the murine insert all gave in vitro transcription products of approximately 800 bases.

A complete amino acid sequence for the cloned human TC-CSF insert is provided in SEQ ID NO: 6. In SEQ ID NO: 6, codons indicated as stop codons in the amino acid sequence of SEQ ID NO: 5 are identified as unknown amino acids ("Xaa").

The nucleotide sequence of murine and human TC-CSF are distinct from the sequence of any other known growth factors. Thus, murine and human genes for a novel growth factor have been cloned.

EXAMPLE 21

TC-CSF Assays

TC-CSF according to the present invention may be the subject of immunoassays, hybridization assays and primer extension assays, such as those using the polymerase chain reaction ("PCR"). Such assays may be used to detect the presence of or site amount of a TC-CSF. By determining the presence or amount of a TC-CSF, diagnosis of conditions characterized by an insufficiency or an excess of TC-CSF is facilitated. Similarly, treatment with TC-CSF may be monitored with respect to attainment or maintenance of a desired level of TC-CSF.

At least one member of a TC-CSF antigen/antibody complex may be linked to a signal molecule which permits detection or quantitative analysis. Polyclonal or monoclonal antibodies or a mixture thereof may be employed in a TC-CSF immunoassay, as may be single chain antibodies, antibody fragments (including Fab fragments), dabs and mabs.

The format of TC-CSF immunoassays may be one-site or two-site ("sandwich"). Sandwich TC-CSF assays may be one-step assays or two-step assays, for example.

Such assays may be prepared in the form of a kit containing an antibody to a TC-CSF and/or TC-CSF lyophilized or in solution in separate bottles. Either a TC-CSF or an antibody thereto may be labeled. A solid support may be linked either to a TC-CSF or to an antibody thereto.

For hybridization assays, probes may be prepared in the form of a kit. Containers including a nucleotide probe complementary in sequence to a TC-CSF polynucleotide (coding or complementary strand) may be labeled and may be prepared in solution or in lyophilized form. Such a probe may be bound to a support, or a TC-CSF polynucleotide may be bound to a support. A probe or a TC-CSF polynucleotide may be bound to a signal or a reporter molecule.

PCR or other primer extension probes for TC-CSF assays may be coding or complementary TC-CSF polynucleotides as described above. Such polynucleotides may be packaged in lyophilized form in a kit.

EXAMPLE 22

Products of In Vitro Transcription and Translation

Further characterization of the murine and human gene inserts was obtained by in vitro transcription and translation. An RNA transcription kit (Stratagene, Catalog #200340) was employed. The RNA transcription kit contains the polymerases, buffers, and ribonucleotides necessary for the in vitro synthesis of RNA transcripts from vectors containing T3 or T7 promoters as is well understood by those skilled in the art. The generated RNA transcripts were translated with an in vitro translation kit (Stratagene, Catalog #200360) in a eukaryotic rabbit reticulocyte lysate, cell-free environment for translating exogenous mRNA into proteins. The exogenous message added to the lysate was translated in the presence of $^{35}$S-methionine which was incorporated in to the newly synthesized proteins. The procedures according to Stratagene technical manuals which accompanied the kits were followed. The expressed proteins were electrophoresed on an SDS-polyacrylamide gel with appropriate controls. The $^{35}$S-labeled proteins were visualized by fluorography. The gel was soaked in Amplify (Amersham, Arlington Heights, Ill, Catalog #NAMP-100), with 2% glycerol for 30 min. and dried. Autoradiography was performed in Kodak developing cassettes using Kodak XAR-5 film (Kodak, Rochester, N.Y.).

The murine gene product exhibited an electrophoretic mobility of 20 to 23 Kd. The human gene product was observed at approximately 11 to 13 Kd.

EXAMPLE 23

Prokaryotic Expression of the Human and Murine Genes

The murine gene and the human gene were expressed in a prokaryotic expression system. Both genes were cloned in the pBluescript™ plasmid as detailed previously. Both inserts may be released from the pBluescript™ plasmid by the cloning site restriction endonuclease EcoRI. A complete vector map is available from Stratagene. Restriction endonuclease analysis of the two inserts was initially performed to determine the restriction sites present within the gene sequences. It was established following restriction enzyme digestion and electrophoresis of the products on 1% agarose gels, that the restriction endonucleases EcoRI, SalI, and BamHI do not digest within the murine or human gene inserts. These enzymes may therefore be used with compatible sites in the polycloning region of other vectors, in order to clone the inserts into appropriate expression vectors. A unique XbaI site is present in the murine gene that gave 0.7 Kb and 1.8 Kb products following digestion with XbaI. The possibility was considered that star activity (non-specific digestion) may be seen with XbaI* on the human gene insert and that star activity may be seen with HindIII* on both the murine and human gene inserts and therefore these enzymes were not utilized for subcloning experiments.

Prokaryotic expression of the murine and human genes respectively, produces recombinant protein when cloned into any of several different expression vectors. This includes the pGEM-4Z™ plasmid (Promega Corporation, Madison, Wis., Catalog #p2161), a vector which allows the synthesis in vitro of RNA transcripts. This vector contains dual opposed SP6 and T7 promoters flanking a multiple cloning site, allowing RNA to be transcribed from either strand of the insert.

The vector allows blue/white color selection for recombinants, by virtue of containing a sequence coding for the lac alpha peptide which, by complementing the product of the host cell lac Z Δ M15 gene, leads to the production of functional β-galactosidase. Bacterial colonies with the lac z gene and also containing a pGEM-4Z™ vector were blue in color when plated on indicator media containing IPTG and X-gal. However, when the lac alpha peptide was disrupted, by cloning into the pGEM-4Z™ multiple cloning region, complementation did not occur and no β-galactosidase activity was produced. Therefore, bacterial colonies harboring recombinant pGEM-4Z™ vector constructs were white.

A complete vector map of the pGEM-4Z™ plasmid is provided by Promega. The murine and human gene inserts may be rescued from the pBluescript™ plasmid following digestion with EcoRI and isolation in low temperature melting point agar. The pGEM-4Z™ vector may be prepared for subcloning by digestion with EcoRI in order to generate compatible ends for cloning the genes. The standard methodology employed was as per Molecular Cloning, A Laboratory Manual, Sambrook et al. eds., Cold Spring Laboratory Press, 2nd edition (1989). Instructions or conditions cited in the accompanying product literature were followed.

The vector DNA was treated with calf intestinal alkaline phosphatase (CIAP) (Promega Catalog #M1821) in order to remove the 5' phosphate groups and prevent recircularization of the vector during ligation. Following incubation with CIAP for 60 min. at 37° C., the reaction was stopped with 0.5 M EDTA, the CIAP and restriction enzyme was removed, and the DNA was purified by phenol extraction and ethanol precipitation prior to ligation. The optimal ratio for ligation of the murine and human inserts to the vector DNA was determined to be 1:1 for the murine insert and 3:1 for the human insert respectively. The ligation reactions were set up with the appropriate ratio of insert to vector DNA, e.g., 1 μg insert DNA with 1 μg vector DNA for 1:1 ratio; and 1 μg insert DNA with 0.3 μg vector DNA for the 3:1 ratio, with: T4 DNA ligase (Promega Catalog #M1801), 1 weiss unit per reaction; ligase 10x buffer, 1 μl per reaction; and deionized water added to bring the final volume to 10 μl. The Ligation reaction mixtures were incubated at 25° C. for 1 hr.

Following ligation, the plasmids containing the murine and human gene constructs respectively were used to transform competent E. coli of the JM 109 strain (Promega), transformation was induced with DMSO and incubation was carried out on ice for 30 min. The resulting E. coli with recombinant constructs were selected by white coloration when plated on indicator media containing IPTG and X-gal. The non-recombinants bacteria were blue.

The recombinant protein was expressed by growing the selected E. coli in LB broth for 24 hours and then adding IPTG to a final concentration of approximately 0.5 mM. The culture was incubated for 3 to 4 hours or overnight to increase the yield of expressed protein.

Following centrifugation, soluble protein was present in the supernatant. Intracellular protein may be extracted from the bacterial pellet by resuspension in buffer (e.g., 50 mM Tris-HCl pH 7.5, 2 mM EDTA, 0.1 M NaCl and lysozyme to a final concentration of 100 μg/ml). Following incubation at 30° C. for 15 minutes the sample may be centrifuged to collect the supernatant containing solubilized protein. The protein may then be subjected to studies by SDS-Page, fractionation and in vitro assays for further characterization.

Prokaryotic expression may also be achieved by cloning the murine and human gene inserts into the $pP_L$ lambda thermoinducible expression vector (Pharmacia, Piscataway, N.J., Catalog #27-4946-010). The phage derived $P_L$ promoter vector may be used for production and manufacture of regulated transcription. However, plasmids carrying the $P_L$ promoter may be unstable due to the high level of transcription. This problem of instability may be overcome by repressing $P_L$ transcription using bacterial hosts that contain an integrated copy of a portion of the phage genome. Such as in E. coli strain N 99 cI+ (Pharmacia) that is a K-12 lambda lysogen. This strain contains the wild type cI+ lambda repressor and may be used for convenient growth of either modified or unmodified $pP_L$ lambda. The host strain used for thermoinducible protein expression for $pP_L$—lambda was E. coli N4830-1 (Pharmacia). This strain carries the temperature sensitive cI 857 lambda repressor and the N genes. The N expression ensures that transcription traverses the entire $P_L$ transcription unit. A complete vector map is available from Pharmacia. Treatment of the EcoRI cloning site of the vector may generate compatible ends with EcoRI digestion and rescue of the murine and human gene inserts respectively. The vector carried Ampicillin resistance gene that may be used for selection of transformed E. coli carrying vectors with constructs. Standard methodology was used as described above. The E. coli carrying the vector may be grown to high density without expression of the cloned gene at low temperature (28° C. to 30° C.) and subsequently induced to synthesize the product at high temperature (42° C.). The soluble protein may be harvested and utilized for further characterization.

EXAMPLE 24

Eukaryotic Expression of the Human and Murine Genes

Eukaryotic expression of the murine and human gene inserts produces authentic recombinant protein when cloned into any of several different expression vectors. This includes the pSV2-neo and subsequent transfection of mammalian cell lines.

The vector pSV2-neo (ATCC 37149) is an expression vector that carries regulatory sequences derived from SV40 while lacking most of the coding region of the viral genome. After transfection into mammalian cells, foreign DNA cloned into these vectors is transiently expressed, however no viral particles are produced. The vector carries ampicillin resistance and neomycin resistance genes and provides dominant selectable markers for resistance to antibiotic G418 in mammalian cell lines. A vector map of pSV2-neo was provided by the American Type Culture Collection and disclosed that it contained a unique EcoRI restriction endonuclease site in pSV2neo compatible with the EcoRI site of the pBluescript™ cloning site that contained the murine and human gene inserts respectively.

TC-CSF gene inserts and the vector may be prepared by digestion with EcoRI, recircularization of the vector DNA being prevented by CIAP as described previously. Following ligation half the plasmids had the inserts in the right orientation.

The recombinant plasmids were expanded in *E. coli* strain HB101 (ATCC 33694) by selection for ampicillin resistance. Plasmid DNA was derived by alkali denaturation and purified by ethidium bromide cesium chloride density gradient. The purified plasmid DNA was used to transfect CHO cells by calcium phosphate-mediated transformation to introduce the foreign DNA into the cultured CHO cells. Care was taken to maintain the pH between 7.2 and 7.28. The pH of the transformation buffer was precisely 7.12. Cultures were maintained at 37° C. in a humidified atmosphere of 5 to 7% $CO_2$ in air.

Successful transformants grew in selective media employing selection for G418 resistance. Clones appeared in 10 to 12 days and were isolated and expanded. The expansion may be done in non-selective media. The supernatant containing the recombinant protein was harvested at 72 hour intervals for six days. Aseptic technique was used throughout. The supernatant was stored at 4° C. and used for further characterization.

EXAMPLE 25

Characterization of the Human and Murine Gene Products

Samples of the gene products from prokaryotic and eukaryotic expression may be run on SDS-PAGE at 0.1% SDS and 16% acrylamide. Samples of mock supernatants derived from cells transformed by vectors without constructs were run with appropriate molecular weight markers in adjacent lanes respectively. Unique protein bands may be seen which bands indicate expression of recombinant protein at 11 to 14 Kd for the human gene product and 20 to 24 Kd for the murine gene product.

The electrophoretic mobility and MW characteristics indicated may vary depending on: the length of the RNA transcripts encoded by the gene inserts; post translational modifications the product may undergo depending on the expression systems used; and whether the expressed protein is a fusion protein or non-fusion protein. Although expression vectors may be selected which are thought to produce non-fusion proteins, nonetheless a gene may be inserted in frame with a leader sequence open reading frame which is unique for the vector. This may result in expression of a recombinant protein which is fused with a small portion of a protein encoded by the leader sequence. This product may have a different electrophoretic mobility and MW compared to the authentic protein produced by in vitro transcription and translation of the gene alone.

The recombinant proteins were used in clonal assays to assess colony stimulating activity on hematopoietic cells. Species specific progenitor cells were used because the colony stimulating activity is usually species specific, for quantifying test results.

Murine bone marrow cells were derived from C57B1 or Balb C. mice and used in agar clonal assays as described previously. The murine gene product when used for colony stimulating activity, at 10% v/v in a 1 ml agar culture gave approximately 6 to 10 CFU-C with $1 \times 10^5$ bone marrow cells. The specific protein concentration was approximately 1 nanogram per ml. Control cultures without colony stimulating activity gave no growth.

Human progenitor cells were derived from bone marrow or peripheral blood samples or normal volunteer donors. The advantages of peripheral blood derived progenitor cells may be considered to be ease of access, and very specific discrimination of progenitor cell proliferation and differentiation in vitro. For example cells such as megakaryocytes are not seen in the peripheral blood and therefore the presence of such cell clusters in, in vitro cultures of peripheral blood derived progenitor cells indicates proliferation and differentiation in vitro from the progenitor cell. Blood samples were collected in heparin from normal volunteers who were not on any medications. The peripheral blood mononuclear cell (PBMC) fraction was collected by harvesting the buffy coat by sedimentation, and then by Ficoll-hypaque (Ficoll-Paque®, Pharmacia, Catalog #17-0840-02) and used for the assay. Each assay employed a 1 ml plasma clot composed of: 10% v/v of, the cell fraction; 0.02 mg L-asparagine; colony stimulating activity; and 4 units of thrombin respectively. Alpha medium (GIBCO) supplemented with 10% human sera was added at 0.5 ml (50% v/v). Human sera was derived from a normal volunteer donor, who had been previously screened to be negative for blood borne infections and who had never received blood transfusions. Blood group type AB donors were used, such that there were no naturally- occurring antibodies, that may interfere with or influence the assay. The mixture was plated and clot formation induced by adding 0.1 ml of bovine citrated plasma. The cultures were incubated at 37° C. in a fully humidified atmosphere of 5 to 7% $CO_2$ in air, for 12 days. The cultures were then evaluated microscopically at 40× magnification for CFU-C. The human gene product gave approximately 3 to 8 CFU-C with $1 \times 10^5$ PBMC from media containing approximately 1 nanogram per ml of specific protein. Control cultures without colony stimulating activity from mock supernatants gave no growth.

EXAMPLE 26

Baculovirus Expression of the Human and Murine Genes

Eukaryotic gene expression may also be accomplished using the Max Bach™ baculovirus expression vector system, for high level of expression of foreign genes. As detailed in the product literature and A Manual of Methods for Baculovirus Vectors and Insect Cell Culture Procedures, Summers et al., Texas Agricultural Experiment Station Bulletin No. 1555, the *Autographa californica* nuclear polyhidrosis virus (AcMNPV) is the prototype virus of the family Baculoviridae. During AcMNPV infection two types of viral progeny are produced; extracellular virus particles and occluded virus particles. These occluded viral particles embedded in polyhedron protein are called polyhedra. The polyhedron protein has a molecular weight of 29 Kd and may accumulate to very high levels. The,polyhedron gene is non-essential for infection or replication of the virus in tissue culture. Inactivation of the polyhedron gene results in production of occlusion negative plaques, which provides a simple way to screen for recombinant viruses in which the wild type AcMNPV polyhedron gene has been replaced with a hybrid gene of choice.

Several transfer plasmids are available (Invitrogen Corporation, San Diego, Calif., Catalog #K822-03). These include fusion vectors with the natural polyhedron leader sequence, such as pAc 360, fusion vectors without the natural polyhedron leader sequence, such as 700, 701 and 702, that differ in the reading frame; non-fusion vectors which have the opposite orientation and also have the natural leader sequence, such as pVL 1392, 1393; and pBlueBac™ non-fusion vector with the natural leader sequence and capable of co-expression of β-galactosidase for color selection. Of these vectors the pVL 1392 and 1393 possess an intact 5' non-coding region, a mutated polyhedron translation initiation codon (ATG to ATT), and a polylinker region that contained a unique EcoRI site. In these vectors, protein translation initiates at a mutated ATG (ATT) if the recombinant gene is inserted in frame with the polyhedron open reading frame. This may result in two recombinant expression products, the nonfused recombinant protein and the recombinant protein fused with polyhedron protein.

The murine and human gene inserts may be rescued by EcoRI digestion and electrophoresis on low temperature melting point agar as described above. The vector may be prepared with EcoRI and recircularization prevented by CIAP. Following ligation, the orientation of the inserts in the plasmid may be checked and the recombinant plasmids purified by cesium chloride ethidium bromide gradient centrifugation.

Plasmids containing foreign genes may be con-transfected with wild type AcMNPV DNA by a calcium phosphate precipitation technique [Graham et al., *Virology*, 52, 456–467 (1973)], modified for insect cells as described below. The foreign gene may be transferred to the AcMNPV genome in a subpopulation of the transfected cells by homologous recombination. For transfection $2 \times 10^6$ Sf 9 cells were seeded in a 25 cm² flask and allowed to attach for approximately 30 min. 1 µg AcMNPV DNA and 2 µg of the plasmid DNA were mixed in a 1.5 ml Eppendorf tube. To this mixture 0.75 ml of transfection buffer (25 mM Hepes, pH 7.1; 140 mM NaCl; and 125 mM $CaCl_2$), may be added and mixed very gently. The media over attached Sf 9 cells may be removed carefully without dislodging the monolayer, and replaced with 0.75 ml Grace's medium containing 10% fetal calf serum and antibiotics (50 µg/ml gentamycin and 2.5 ml amphotericin B). The DNA solution may then be added dropwise to the cells and the flask incubated at 27° C. for 4 hours. Following incubation, the supernatant medium may be removed and the cells rinsed with fresh complete TNM-FH (i.e., Grace's insect medium plus supplements plus 10% fetal bovine serum), then 5 ml of complete TNM-FH may be added and the cells incubated for 5 days at 27° C. Successful transfection may be assessed by visualizing the cells after the incubation on an inverted microscope at 250× to 400× magnification. About 20 to 50% of the cells may contain viral occlusions that appeared as refractive crystals in the nucleus of the insect cell. The cells may also appear increased in size and there may be evidence of cell lysis. The supernatant media from the transfection experiment may be used in a plaque assay to test for recombinant virus.

For the plaque assay $1.75 \times 10^6$ Sf 9 cells may be seeded in to 60×15 mm culture plates in complete TNM-FH medium. The cells may be allowed to attach for approximately 30 min. Ten-fold dilutions ($10^{-3}$ through $10^{-5}$) of the virus inoculum may be made in TNM-FH, allowing approximately 1 ml of viral dilution for each plate; Cell attachment to the culture plates may be confirmed by microscopic examination.

The supernatant media may be removed carefully, without disturbing the monolayer and replaced with 1 ml of diluted virus inoculum. The plates may then be incubated at 27° C. for 1 hour. An agarose overlay may be prepared at 5 ml per plate. For each plate, 0.075 g low melting point agarose may be added to 2.5 ml distilled water and autoclaved for 10 to 15 min and equilibrated at 42° C. To each 2.5 ml of agarose may be added 2.5 ml of the media mixture (2 ml of 2× TNM-FH, and 0.5 ml fetal calf serum and antibiotics, equilibrated to 42° C.), after removal of the virus inoculum from the culture plates 4.5 ml of the agarose overlay mixture may be added to cover the cell monolayer. The agarose may be allowed to solidify at room temperature for 30 min and then incubated for 5 days at 27° C. in a humidified atmosphere.

Plaques may be well formed in five days and recombinant plaques may be identified as being occlusion negative plaques due to the presence of recombinant virus. The plaques may be isolated by removing them and the agarose plug directly over the plaque with a pasteur pipette. This may be transferred in to a tube containing 1 ml of fresh TNM-FH medium. Plaque purification may be done ×2 or ×3 by passaging each plaque isolated on separate monolayer cultures. After two passages viral stocks may be prepared by inoculating 1 ml of the recombinant virus in a total inoculum of 5 ml to infect $2 \times 10^7$ Sf 9 cells in a T-150 flask. Following a one hour absorption period an additional 20 ml of complete TNM-FH media may be added and virus harvested three days post infection. This supernate may be stored for stock following centrifugation of the suspension. The cells and supernate may be collected separately. The supernate may be rendered free of virus by ultracentrifugation at 100,000×g for 30 min at 4° C.

EXAMPLE 27

Purification of TC-CSF

Purification of the recombinant protein may be performed following prokaryotic or eukaryotic expression according to standard methodology [Scopes, Protein Purification: Principles and Practice, 1982, Springer-Verlag, N.Y. (1982); *Methods in Enzymology*, 22, 233–577 (1971)].

Purification of the protein in solution may be done in serial, stepwise stages. Initially quaternary aminoethyl ("QAE") column chromatography may be used, the QAE column may be equilibrated with at least three column volumes of 20 mM Tris-HCl at pH 7.5. The pH of the TC-CSF-containing supernate or extract may be adjusted to pH 7.5 with sodium hydroxide or hydrochloric acid, and applied to the column. The column may be eluted in a sodium chloride gradient of 0 to 0.5 M in the 20 mM Tris-HCl buffer for about ten column volumes. The TC-CSF containing fractions may be identified by SDS-PAGE and then combined and concentrated by ultrafiltration (Amicon) with a membrane having a 3000 to 5000 MW cut-off. The protein in the concentrate was precipitated by 60 to 70% ammonium sulphate and collected by centrifugation. The precipitate may be washed with 20 mM Tris HCl at pH 7.5 containing 60 to 70% ammonium sulphate. The precipitate may be collected by centrifugation and then redissolved in 20 mM Tris-HCl at pH 7.5. The solution may be filtered through a 0.22µ filter and loaded onto a Sephadex G-100 column equilibrated with 20 mM Tris-HCl, pH 7.5. The column may then be eluted with the same buffer and the fraction collected. The protein-containing fractions may be identified by SDS-PAGE and combined.

Following filtration through a 0.22µ filter the filtrate may be applied to a reverse phase high pressure liquid chromatography ("rpHPLC") column. The column may be equilibrated with 1% trifluoroacetic acid that then eluted with an acetonitrile gradient of 0 to 100% dissolved in 0.1% trifluoroacetic acid. The fractions may be collected and may be combined based on SDS-PAGE MW estimations expected from the expression system used. All fractions may be retained and reprocessed in order to increase recovery. The pooled fractions were dialyzed against 20 mM sodium phosphate at pH 7.2, with two buffer changes at four to five hour intervals by ultrafiltration with a 3000 to 5000 MW cut off membrane. The concentrate was then filtered through a 0.22μ filter and then may be used for further studies or stored at −20° C.

Variations in the purification procedure may be introduced depending on the source of the recombinant protein and growth medium and supplements used for the expression system. Certain purification steps may be repeated in order to have a satisfactory product for that step in the process. Modifications may be introduced in order to obtain the best yield of the product and retain optimal activity.

EXAMPLE 28

Analysis of the Murine TC-CSF Nucleotide Sequence and Protein Molecule

Analysis of the murine TC-CSF protein molecules and nucleotide sequences, suggests that there are at least two forms of the protein. One is the large 55 Kd molecule that may be expressed from the EL-4 cell line by PMA stimulation. Amino acid sequencing of this protein and comparison with the nucleotide sequence of the murine DNA clone suggests that the transcription is initiated at the first Met and proceeds sequentially as shown in SEQ ID NO: 2. This is the derived amino acid sequence from the nucleotide sequence given in SEQ ID NO: 1. The sequencer derived amino acid sequence of the 55 Kd protein molecule is given in Table 2, supra.

The existence of a second form of TC-CSF protein is supported by expression data, i.e., a protein having a smaller size of approximately 23 to 24 Kd. Analysis of the nucleotide sequence revealed that the first Met was either not present in the DNA strand or was being lost by digestion with the cloning site restriction enzyme EcoRI, together with several more bases during the subcloning procedures. Initiation of protein synthesis therefore had to occur at an internal Met site, most probably the second Met at position 161 SEQ ID NO: 2. Subsequent to this Met, at position 168 there is a termination codon denoted as Xaa, with the next termination codon at position 189. Since this DNA sequence is derived from hnRNA, sequences that are transcribed and untranscribed in mRNA are present in this DNA sequence. Demarcations of the regions may be indicated by the termination codons. The sequence of 20 to 25 predominantly hydrophobic amino acids typical of a signal or leader peptide sequence of a secreted protein contained between the termination codon at position 168 to the next stop codon at position 189 may represent an untranscribed region, this is followed by a transcribed region from position 190. Following cleavage of this leader peptide from the secreted protein that may be expressed from the transcribed regions of the DNA clone, it would be consistent for the expressed protein to be around 23 Kd in MW and not 55 Kd. Since bioactivity is retained, the smaller protein molecule is encoded by the bioactive region, while the larger molecule contains the bioactive region together with an unusual amino terminus sequence.

The findings and analysis are analogous to studies with GM-CSF and IL-3, where it is apparent that multiple forms of mRNA exist for the colony stimulating factor genes. This has been demonstrated from studies of GM-CSF and its transcripts, Stanley et al., *EMBO J.*, 4, 2569 (1985).

Expression of the murine insert in the pSV2-neo vector following subcloning at the EcoRI site suggests that the murine insert has its own promoter sequences, or cryptic promoters within the expression system used. Since at the EcoRI site the gene is not under influence of the SV40 promoter. Analysis of SEQ ID NO: 1 reveals a GC rich region associated with CAAT stimulating sequences and sequences encoding TATA in the upstream region. However the promoter may be weak compared to the SV40 promoter, and the poly A addition may not be efficient, hence the weak expression. Expression data support the concept that the murine insert is a single gene with the DNA sequences being derived from hnRNA with the termination codons indicating transcribed and untranscribed regions, within portions of DNA. The expression data also supports the concept that the murine TC-CSF is a monocistronic product.

EXAMPLE 29

Analysis of the Human TC-CSF Nucleotide Sequence and Protein Molecule

The human TC-CSF coding sequence is contained at least partly in a 800 base pair insert. The sequence of 630 bases of this insert is given as SEQ ID NO: 5. Further sequencing of the insert gave an additional 30 bases upstream at the 5' end. This additional sequencing revealed that the 800 base pair insert contained a non-coding region of 45 bases upstream of the initiating ATG, up to the cloning site restriction enzyme EcoRI site. The initiating ATG for TC-CSF is located at positions 16–18 encoding amino acid 6 (SEQ ID NO: 5). Between nucleotide positions 55–84 are codons for predominantly hydrophobic amino acids consistent with identity as a signal peptide sequence. Following cleavage of this leader peptide up to a polar uncharged tyrosine, the subsequent sequence from nucleotides at positions 85–177 demonstrates strong homology with the murine sequence contained between nucleotide positions 843–1150 of the murine sequence (Table 3).

Subsequent to these regions there is no apparent homology between the murine and human TC-CSF sequences. Searches through databanks including Genebank reveals that, within a portion of the 800 base human insert, there is homology with human thioredoxin protein. The homology starts in the human TC-CSF sequence at nucleotide 170 and extends to nucleotide 630. The thioredoxin protein is a heat stable redox protein that functions as protein disulphide reductase. No hematopoietic growth promoting activity has been attributed to the thioredoxin protein. Evidently there are two distinct proteins that are being encoded as a fusion product in the 800 base pair human insert. Since the first 170 nucleotides of the TC-CSF gene sequence that contain the initiating ATG (at nucleotide positions 16–18), the signal peptide sequence (at nucleotide positions 55–84) and the region of homology with the murine gene (at nucleotide positions 85–170) is absent from the known thioredoxin protein sequence. The earliest initiating ATG for the thioredoxin protein corresponds to nucleotide positions 227–229 of the 630 base sequence given for TC-CSF. This indicates that at the bases at positions 1 to 226 of the 630 bases do not encode for the thioredoxin protein per se. A gene insert in a cDNA library that encodes for the combined sequences of two protein molecules may be that the fusion occurred during construction of the library. The incidence of two gene sequences linking together without an intervening termination codon has been indicated to be small. Nonetheless it does occur.

Two clones may be ligated to each other. When first and second strands are synthesized, then the strands are blunt ended and the cDNA's are methylated and added to polylinkers for ligation. During the ligation reaction, instead of the polylinkers linking to individual clones, two pieces of DNA may be ligated. This linkage may occur, especially under conditions where clones are selected to have a size of 600 bases or greater as in the present case.

Thus, the small TC-CSF gene of approximately 200 bases may have been ligated to another gene. The ligation may have occurred either directly, blunt end to blunt end, or through a small intervening piece of polylinker. The latter is considered since the cloning site restriction enzyme for the library is EcoRI and is present on either end of the insert. The sequence at the site where the two genes may have fused is TTGGATCCA. These nine bases have eight restriction enzyme sites on them namely, BIN 1, XHO 2, BAM 1, NLA 4, MBO 1, DPN 2, DPN 1, and BIN 1. Therefore, ligation may be produced a fusion clone that was carried as a single insert linking the two genes at the cloning site.

Confirmation of the hematopoietic activity of the human TC-CSF sequence and results distinguishing it from the thioredoxin protein were obtained by restriction enzyme digestion of the insert in the region after nucleotide 177 to separate the sequence encoding for TC-CSF and by subcloning into an expression vector.

Restriction enzyme analysis of the 800 base pair human clone had revealed the unique BamHI site at the site of linkage of the TC-CSF gene and thioredoxin gene sequence. BamHI did not cut within the human gene sequence and was used to separate the two sequences. The restriction enzyme digestion was done with 0.5 units/µg DNA with the recommended BamHI reaction buffer (150 mM NaCl, 10 mM Tris-HCl, 10 MM $MgCl_2$ 1 mM dithiothreitol-pH 7.9 at 25° C.), supplemented with 100 µg/ml bovine serum albumin and incubated at 37° C. Samples were examined by agarose electrophoresis for restriction fragments. Following digestion and electrophoresis, the restriction fragments were a 200 base fragment containing the unique TC-CSF portion and a 600 base fragment that was homologous with thioredoxin.

The 200 base fragment encoding human TC-CSF had EcoRI restriction site at the 5' end and BamHI on the 3' end. This fragment was subcloned into the Baculovirus expression vector pVL 1392. The vector pVL 1392 possess an intact 5' non-coding region, a mutated polyhedron translation initiation codon (ATG to ATT), and a polylinker region that contained an EcoRI site nearer to the vector 5' end and BamHI site near to the vector 3' end. Thus the TC-CSF fragment may be inserted by directional cloning in the right orientation. In this vector protein translation may initiated at the mutated ATG if the recombinant gene is inserted in frame with the polyhedron open reading frame or at the initiating ATG in the insert. This may result in two recombinant expression products: the non-fused recombinant protein and the recombinant protein fused with polyhedron protein. The vector may be prepared by digestion with EcoRI and BamHI in order to receive the compatible ends of the insert, following ligation the orientation of the insert may be checked. The control vector was one in which no gene construct was inserted. The plasmids were purified by cesium chloride and ethidium-bromide density gradient centrifugation. Co-transfection of the insert cells with the insert-containing plasmid and control plasmid respectively were done with wild type AcMNPV DNA, by the calcium phosphate precipitation technique as detailed in Example 26. Recombinant plaques may be identified as occlusion negative plaques. The supernate from these and control plaques were collected and tested for bioactivity in CFU-C clonal assays. Additional material used as controls were polyhedron protein, and the AcMNPV transfected insect cell culture media.

The bioactive supernate was run on SDS-Page to identify a recombinant protein band. However no recombinant protein band was clearly discernible. It should be noted that this recombinant protein would be expected to run at an electrophoretic mobility of 3 to 3.5 Kd in comparison with molecular weight markers. It was concluded that the concentration of the recombinant protein was less than 10 ng/ml. The activity is potent, because the supernatant may be associated with colony stimulating activity of 4 to 6 CFU-C, when 0.1 ml of the supernate was used in 1 ml culture to assess the growth activity. Control cultures such as the mock supernate or polyhedron protein or AcMNPV-transfected insect cell culture media gave no growth of CFU-C.

EXAMPLE 30

Construction of a Synthetic TC-CSF Gene

Several improvements may be made towards expression of an optimal product by synthesis of an artificial gene. The techniques for the construction and expression of synthetic genes are well established: e.g., Sproat et al., *Nucleic Acid Res., 13,* 2959–2977 (1985); Gait, *Oligonucleotide Synthesis: A Practical Approach*, IRL Press, Oxford, U.K. (1984); Ferretti et al., *Proc. Nat'l. Acad. Sci. (USA), 83,* 599–603 (1986).

A synthetic gene for TC-CSF may be constructed in view of the following considerations. The initiating ATG in the TC-CSF sequence is 45 bases downstream from the 5' end and EcoRI site where the insert sequence was digested from the polylinker of the vector. Promoter sequences in expression vectors into which the TC-CSF gene is inserted may be weakened by having 45 non-coding bases intervening before the initiating ATG. Furthermore, during expression in vectors that possess a translation initiation codon, the inserts non-coding region may be translated into a coding region. Depending on the reading frame selected, the translated intervening region may now code for a translation termination codon, thus preventing further translation of the coding sequence. In the synthetic gene the non-coding region may be shortened and the initiating ATG placed nearer to promoter sequences such that strong expression ensues.

Another example for improvement by constructing a synthetic gene is by addition of a termination codon to a TC-CSF portion of an insert. Because, following digestion of the 800 base pair insert with BamHI in order to separate the TC-CSF sequence from the thioredoxin sequence, the 3' end of the TC-CSF contained a BamHI site but did not contain a termination codon. For appropriate expression the 3' end had to be engineered to either have a termination codon attached or use of the vector sequences that translate into a termination codon in the appropriate reading frame. In the latter case some amount of vector protein is fused to the TC-CSF protein. This protein is unnecessary and is preferably avoided. Adequate and appropriate unique restriction enzyme sites may not be available in the isolated cDNA insert in order to enable the accomplishment of all planned improvements and thus the synthetic gene would be advantageous for the production of an optimal product.

The synthetic fragments are synthesized using standard techniques, preferably an automated synthesizer is used such as, Applied Biosystems Inc., model 380A (Foster City, Calif.). Base sequences for the synthetic gene were selected such that the assembled synthetic gene contained the desired coding segment with an optimally situated initiating ATG at the 5' end and a translation termination codon at the 3' end. Base sequences were designed encoding for unique restriction enzyme sites at both ends, with respect to the desired vectors that may carry the gene or express the gene. Unique restriction enzyme sites may be designed within the gene such that segments of the gene, defined by the unique restriction sites may be excised and replaced with segments having altered base sequences. This enables the construction of mutants; production of mutant gene products; and specific partial products, etc., all of which may have medical and scientific applications.

The nucleic acid cassette consists of the double stranded DNA fragment encoding for the bioactive portion of TC-CSF. For example the portion that constitutes the sequence between nucleotide positions 16 to 177 as shown in SEQ ID No: 5. This coding sequence is flanked by linkers at each end. The linker for the 5' end and the 3' end may have base sequences for unique restriction enzyme sites selected for compatibility for directional cloning with the 5' end and 3' end respectively of the desired expression vector or carrier vector.

A wide selection of synthetic linkers coding for any selected restriction endonuclease are available from: Midland Certified Reagent Co., Midland, Tex.; Research Genetics, Huntsville, Ala.; Lofstrand Laboratories, Gaithersburg, Md. These custom laboratories synthesize the complete gene cassette with the linker ends according to specifications under contractual agreement.

EXAMPLE 31

Construction of a Synthetic TC-CSF Peptide

Expression of the TC-CSF portion of the gene insert gave a bioactive recombinant protein as described in the previous example. Analysis of the nucleotide sequence and partial amino acid sequence revealed that the expressed recombinant protein may have a sequence (as given in SEQ ID NO: 7) of:

```
Amino
Terminus
          Y W T F V I K I N L F Y N S N
          S P V W K K K Q P A L F G A L   Carboxy
                                          terminus
```

For further confirmation that the amino acid sequence was the bioactive sequence, a synthetic peptide was synthesized.

The methodology for solid phase peptide synthesis is well established and has achieved universal acceptance. Fluorenylmethoxycarbonyl (Fmoc) protection for the alpha amino group and the development of supports, active esters and activation strategies have improved the methodology considerably. Chang et al., *Int. J. Pept. Protein Res., 11,* 246–249 (1978); Atherton et al., *J. Chem. Soc. Chem. Commun., 3,* 165–166 (1985); Hudson, *J. Org. Chem., 53,* 617–626 (1988). For the synthesis, an automated peptide synthesizer such as the Advanced Chemtech, model MPS 350 (Louisville, Ky.), may be used. The steps in the synthesis for a cycle and methods used are discussed.

In the coupling procedure, the activation was done using diisopropylcarbodiimide (DIPCDI) and 1-hydroxybenzotriazole (HOBt), by this combination the efficiencies of coupling are reported as 1.33 times that observed with symmetrical anhydrides and gave cleaner products. The practical value of DIPCDI and HOBt is further enhanced by the lack of racemization using this method. Double coupling may be used, increasing the efficiency. An optional capping may be performed with acetic anhydride and pyridine. Under most circumstances, however, the high efficiency of the Fmoc chemistry eliminates the need for capping. Deblocking, that is the removal of the Fmoc protecting group may be done by treatment with the secondary amine piperidine. The gentle deblocking conditions are an important advantage of the Fmoc method. After the deblocking step has been done, the cycle is repeated. The peptide may then be cleaved and deprotected using Trifluoroacetic acid (TFA), a relatively mild organic acid, with scavenger reagent R. (Research Genetics, Huntsville, Ala.).

The preparative peptide purification by HPLC was done in a C 18 preparative column in TFA-acetonitrile system, with Waters Delta Pak (Millipore Corp., Waters Division, Marlborough, Mass.) The column specifications were 25×30 mm, 15$\mu$; the conditions were A=0.1% TFA; B=0.1% TFA in acetonitrile. The gradient was 0–60% B at 1% per minute.

Analytical HPLC may be done using a Vydac column with the specifications of: C 18, 4.6×250 mm 5 $\mu$m 300 Angstrom (Vydac Hesperia, Calif.). The conditions may be A=0.1% TFA, B=0.1% TFA in acetonitrile, the gradient was 0% B for 3 minutes, then 0–60% B in 27 minutes. The UV detector was set at 210 nm. The HPLC chromatogram of the product was consistent with more than 80% purity, with a single peak indicating homogeneity of the assembled 25 residues. The synthetic peptide may then be lyophilized.

In accordance with recommendations, the length of the peptide was limited to 25 residues. The amino acid sequence [SEQ ID NO: 8] of the selected peptide was: YFVIKINLFYNSNSPVWKKKQPALF with the initial tyrosine being acetylated and the terminal phenylalanine being amidated. The initial tyrosine was retained to precede the phenylalanine, in order to facilitate labeling with radioactive iodine. The radiolabeled product may be used to investigate the TC-CSF receptor, for investigation of the mechanism by which the action of TC-CSF is mediated or in assays as a competitor for TC-CSF. Further variations in the synthetic peptide include one or more amino acid substitutions or deletions at various positions, such that new improved molecules are available and the effect of the substitutions on disease states may be investigated.

The biological activity of the synthetic peptide was assessed by in vitro clonal cell culture assays, similar to the clonal assays described previously such as in Example 2. Unlike the procedure of Example 2, however, methyl cellulose was employed as the semi-solid matrix supplemented with alpha media (GIBCO), and 30% fetal calf serum. This culture system allows the assessment of CFU-C, CFU-M, as well as BFU-E. The colony stimulating activity for CFU-C and CFU-M being provided by the TC-CSF in test cultures and recombinant IL-3 (GIBCO) in control cultures. For the stimulation of BFU-E growth, 1 unit of recombinant erythropoietin (Amgen, Thousand Oaks, Calif.), was added to each 1 ml culture. The human CFU-C cultures were incubated for 14 days at 37° C. in a humidified atmosphere of 5 to 7% $CO_2$ in air.

In the test cultures the synthetic peptide was assayed at concentrations expected to range from approximately 3 units to 100 units of activity. The results of the control cultures with 100 units of recombinant IL-3 were compared with those of the synthetic peptide, expected to have approximately 100 units of activity and are given below. The results with IL-3 are given in parenthesis alongside those of the synthetic peptide. The CFU-C assay was done with $5\times10^4$ human bone marrow cells per culture colony stimulating activity was seen with colony formation of: BFU-E 38 to 47 (IL-3, 52 to 77); CFU-GM 15 to 18 (IL-3, 37 to 47); CFU-M 2 to 3 (IL-3, 2 to 3); CFU-F 3 to 4 (IL-3, 2 to 3); lymphocytes 3 to 4 (IL-3, 1 to 2).

Growth activity of the synthetic peptide was approximately 30% to 40% of that expected with a similar concentration of recombinant hematopoietic growth factor. The explanation for this may be multifactorial, in that the synthetic peptide had 80% purity, trace amounts of the chemicals used may be present causing growth inhibition; the synthetic peptide is exquisitely sensitive to proteases that may be present in the tissue culture system with consequent growth inhibition by abrogation of growth stimulatory properties; the secondary structure and stoichometric configuration of the synthetic peptide may not be identical to the biological product and may not conform to that required for greater bioactivity. Since the entire spectrum of colony stimulating activity was present and morphological examination of the CFU-C revealed extremely healthy appearance, it may be concluded that the portion of the synthetic peptide that was bioactive retained optimal functional properties. While there was a large component being synthesized, that was non-functional and inert for bioactivity in the clonal assay system used, or being rendered thus by the action of proteases or traces of impurities. Potency of the synthetic peptide may be increased if all the amino acid residues of the bioactive moiety of the biologically-derived protein were assembled sequentially instead of the modified sequence of 25 amino acids.

Improvements in the process of peptide synthesis and composition will be considered and implemented. Nonetheless the dose response assay established increasing growth stimulatory activity commensurate with increased dosage. Colony stimulating activity was seen with an increase in the number of colonies of BFU-E (erythroid); CFU-GM (granulocytes and macrophages); CFU-M (megakaryocytes); CFU-F (fibrocytic stromal cells); and those of the lymphocytic lineage.

It is concluded that the nucleotide sequence for TC-CSF, encodes a protein, the amino acid sequence of which protein has multipotential growth stimulating activity.

EXAMPLE 32

Analysis of TC-CSF Antigenic Determinants and TC-CSF Antibodies

In order to further evaluate the amino acid sequence of the TC-CSF, a computer analysis was done for the prediction of antigenic determinants. The method used was that of Hopp et al., *Proc. Nat'l. Acad. Sci. (USA), 78,* 3824–3828 (1981). As recommended by the authors the averaging group length was six amino acids, and the average hydrophilicity points were noted. The three highest points of hydrophilicity were ranked.

```
1.    Average hydrophilicity value 1.45 for
      amino acids 48-53 (SEQ ID NO:14) in SEQ ID
      NO: 6:
      K   K   K   Q   P   A
      Lys Lys Lys Gln Pro Ala 2.    Average hydrophilicity value 0.62 for
      amino acids 33-38 (SEQ ID NO:15) in SEQ ID
      NO: 6:
      V   I   K   I   N   L
      Val Ile Lys Ile Asn Leu 3.    Average hydrophilicity value 0.08 for
      amino acids 13-18 (SEQ ID NO:16) in SEQ ID
      NO: 7:
      N   S   N   S   P   V
      Asn Ser Asn Ser Pro Val
```

It should be noted that on a group of control proteins the highest point was assigned in 100% of the cases to a known antigenic group, indicating the predictive value of the highest point. The second and third points gave a proportion of approximately 67% of correct predictions and 33% incorrect predictions.

Because the synthetic peptide is bioactive, it may be used to raise specific antibodies to bioactive sites of TC-CSF, and these, antibodies may be polyclonal or monoclonal. The techniques for producing monoclonal antibodies are well established, e.g., Kohler et al., *Nature, 256,* 495 (1975); Kohler, in: *Immunological Methods,* eds. Lefkovits et al., Academic Press, New York, N.Y. (1979). The immunogenic regions of the TC-CSF molecule have been analyzed by prediction of antigenic determinants and ranked for hydrophilicity. Antibodies may be raised to the corresponding regions and used to facilitate the design of diagnostic or therapeutic agents.

EXAMPLE 33

Polyethylene Glycol and TC-CSF Conjugation

Therapy with protein molecules may be associated with side effects, that may be increased in magnitude with the parenteral mode of therapy. some of these problems may be secondary to short circulating half life of the protein, such that high doses may be necessary to achieve efficacy and quite often frequent doses may be required. Other side effects may be caused by the immunogenicity of the protein giving rise to allergic manifestations or hypersensitivity reactions. It is advantageous to be able to extend the life of the therapeutic protein and reduce the immunogenicity.

The addition of polyethylene glycol (PEG) to therapeutic proteins is well established, e.g., Lundblad et al., in: *Chemical Reagents for Protein Modification,* CRC Press, Boca Raton, Fla. (1984); Zalipsky et al., *Biotechnology and Applied Biochemistry, 15,* 100–114 (1992), Berger et al., *Blood, 71,* 1641–1647 (1988). The addition of PEG to proteins may prevent or delay their recognition by the immune system, thereby lowering immunogenicity. Furthermore, PEG-protein conjugates when injected into animals have been shown to circulate longer than the unconjugated protein. Thus extending the life span of the protein and possibly reducing the total dosage required.

TC-CSF-PEG conjugates may be effective by circulating longer and thereby reducing the dosage required. In addition the TC-CSF and PEG conjugate may be less immunogenic, when used for therapy and thus reduce side effects if any occur.

Based upon the above results, it is submitted that a novel growth factor molecule was synthesized from T lymphocytes. The growth factor stimulated the growth of multipotential hematopoietic progenitor cells. The growth factor protein was isolated and a partial amino acid sequence derived. Oligonucleotide probes were constructed encoding the partial amino acid sequences of TC-CSF and the gene for the growth factor molecule cloned. The nucleotide sequence for the gene confirms that this is a novel growth factor molecule. No real homology was demonstrable with any other known growth factor molecule.

Considerable evidence exists that T lymphocytes are essential for the regulation of proliferation and differentiation of hematopoietic progenitor cells. Stimulation by phorbol esters or lectins of human T cells such as the Jurkat cell line produces T cell derived growth factor that stimulates hematopoiesis under controlled conditions such as in vitro plasma clot cultures. Although specific colony stimulating factors such as IL-3 and GM-CSF that have multi-lineage hematopoietic colony stimulating activity may be produced by T lymphocytes, the most potent source of IL-3 and GM-CSF is not T cells. Furthermore, evidence is available from clinical observation of patients with T cell deficiencies, such as in AIDS, that an initial response with improvement in blood counts to therapy with IL-3 or GM-CSF is usually not sustained. The response can recur if there is an improvement in T cell status, thus indicating that a T cell derived factor is necessary for hematopoiesis that is distinct from IL-3 or GM-CSF.

The possibility is considered that mutations in other portions of the sequence may code for an amino acid including the amber mutation TGA that may code for Cys or Trp.

The above data and Examples establish that the TC-CSF is a novel hematopoietic growth factor. Potential uses for TC-CSF include: 1) delineation of the regulation of hematopoiesis; 2) identification of disease states in which de-regulation occurs; 3) stimulation of hematopoiesis (this may be in vitro or in vivo, particularly in patients who may have suppression of hematopoiesis either due to disease or secondary to chemotherapeutic agents being used for treatment of a malignancy); 4) gene therapy where introduction of this gene into cells may have beneficial effects; 5) other uses may be considered, such as treatment of immunocompromised patients who concomitantly have low blood counts; and stimulation of hematopoietic cells into a cell cycle phase such that cell cycle phase specific chemotherapeutic agents may then act more effectively.

TC-CSF stimulates the growth of fibrocytic stromal cells. These cells give rise to the hematopoietic microenvironment that is essential for the maintenance of hematopoietic progenitor cells, their proliferation and differentiation. Clinical use of the growth factor is useful in reconstitution of the microenvironment and restoration of function, in those desease states in which it may be affected.

TC-CSF stimulates the growth of cells of the lymphocytic lineage. There are indications that the growth factor may stimulate pre-B lymphocytic cells. Immune reconstitution and restoration of immune function may be considered for the therapeutic use of the growth factor.

The bioactive moiety of the TC-CSF is a very small molecule. Bioactivity of the synthetic peptide demonstrates that broad spectrum growth stimulatory activity may be encoded by 25 to 30 amino acid residues that constitute part of the TC-CSF sequence. The small size would be consistent with reduced side effects particularly with parenteral therapy, with consequent reduction in risk factors while maintaining high therapeutic benefit. In view of this and the broad spectrum growth stimulatory properties of the TC-CSF the aforementioned therapeutic uses are merely to indicate some desease entities in which the product may be considered as a therapeutic agent. The use is not intended to be restricted exclusively to these groups. On the contrary, treatment would be extended for any disease state where the product may be beneficial, subject to regulatory guidelines of agencies appointed for this purpose. These are agencies such as the FDA in USA and like agencies in other parts of the world.

The possibility is considered that the TC-CSF gene may be a regulatory gene, that may regulate the transcription of other growth factor genes. In that case there may be considerable potential in utilization of the TC-CSF gene for gene therapy.

The specifications of the least degenerate oligonucleotide probe for screening were ACNATGCCNGAPGAYGC (SEQ ID NO: 18), where Y=pyrimidinee; P=purine; N=any base. The rationale for oligonucleotide selection was based upon the N-terminal peptide sequences previously given in Table 2 of the disclosure. The region selected, for construction of the probe being from amino acid No. 9 through No. 15, i.e., Asp-Thr-Pro-Met-Pro-Glu-Asn or Lys. In order to reduce codon bias and the number of permutations, construction of the 17 mer probe from this sequence was based upon the selected peptide encoded by residues Asp-Thr-Met-Pro-Glu-Asn, as previously disclosed in SEQ ID NO: 4. The 17 mer probe had less than 1:64 permutations and was used to screen the library constructed from Poly(A)+ RNA of EL4 cells converted to double stranded cDNA, with size selected cDNA strands of more than 2.0 Kb capable of encoding a protein of MW 55 Kd. The labeled probe hybridized under stringent conditions to the clone that was designated cc2, the nucleotide sequence of which was given as SEQ ID NO. 1 and the deduced amino acid sequence as given as SEQ ID NO. 2. The deduced amino acids No. 9 through No. 15 in the clone were Asp-Thr-Pro-Val-Pro-Glu-Lys and contain those from which the probe was constructed. As was considered in the disclosure the nucleotide sequence for amino acid No. 12 was GTG, that may encode Met or Val. Thus it was apparent that strong homology exists between the predicted murine full length protein and the isolated murine TC-CSF or model N-terminal sequence used to prepare the probes and is considerable enough to allow one with ordinary skill in the art to accomplish the cloning of the gene, as has been demonstrated by this invention. With respect to the 554 residue nucleotide sequence, when appropriate corrections are made for water ($H_2O$) and sulphur bonds composing the molecule that contribute to the molecular mass determined from amino acid composition, as compared with specific electrophoretic mobility this composition is consistent with a molecular weight of 55 Kd by gel electrophoresis. The experimental determination of amino acid composition as given in Table 1 and partial amino acid sequence of TC-CSF as given in Table 2, were determined by sequencing the native protein with bioactivity and specific electrophoretic mobility of 55 Kd. As detailed in Example 5 and 9, the specific TC-CSF protein of MW 55 Kd was isolated following gel electrophoresis and blotting onto a PVDF membrane; the 55 Kd band identified by Coomassie blue staining and excised for sequencing.

Thus enabling isolation and characterization of the specific 55 Kd protein, determination of the N-terminal sequence, construction of less degenerate oligonucleotide probes and isolation of the clone. The nucleotide sequence (SEQ ID NO: 1) and deduced amino acid sequence (SEQ ID NO: 2) determined for the insert of clone CC2 have strong identity with the experimentally determined amino acid composition given in Table 1 and the amino acid sequence given in Table 2 of the disclosure. Thus providing cogent evidence that this was the encoding nucleotide sequence for the 55 Kd protein isolated from the PMA conditioned EL4 cells.

The insert isolated from clone CC2 was labeled and used to screen the library constructed from Poly(A)+ RNA of the Jurkat T cell Leukemia cell line, following conversion to double stranded CDNA, with size selected CDNA strands of less than 800 bases preponderantly derived from late mRNA that may encode biologically active humoral proteins. The labeled cDNA insert derived from EL4 T cells, encoding the 55 Kd TC-CSF, hybridized under stringent conditions to a cDNA clone of the Jurkat T cell library, thus establishing strong and specific identity between the two cDNA inserts. The insert-containing clone isolated from the Jurkat cell library was designated CC7, the nucleotide sequence of which was disclosed as SEQ ID NO: 5.

Regarding the human TC-CSF cDNA sequence disclosed as SEQ ID NO: 5, this has been modified upon consideration of resequencing, and amino acid sequencing of the encoded protein. Thus the triple codon at position 55 that was read as an ochre mutation TAA, is corrected to TAT or TAC or Tyr. The triple codon at position 87 that was read as TAG, an amber mutation may be TCG (Ser) or TGG (Trp). Analysis of the amino acid sequence suggests this amino acid may be Trp. This amino acid may be Trp. For the purpose of this application it is considered as TGG (Trp), however amino acid sequence heterogeneity may occur at this site, that is the NH$_2$-terminus of the serrated protein following cleavage from the signal peptide. The triple codon at position 129 was read as TGA (Ser). Analysis of the amino acid sequence suggests this may be Ser.

Translation of mRNA in vitro has been demonstrated to initiate at the first AUG in preference to the second or third. Furthermore it is known that in 95% of eukaryotic mRNAs translation begins at the AUG codon closest to the 5' end of the mRNA. Therefore the initiating Met for the unique TC-CSF is at pos 16 of SEQ ID NO: 5. As detailed in Example 29 following cleavage of the CDNA by restriction enzyme BamHI into the unique 200 base pair fragment that encodes TC-CSF and the 600 bp fragment that encodes thioredoxin, the 200 bp fragment was expressed and the product was analyzed. It is noteworthy that the human nucleotide sequence, at positions 85–177 demonstrates strong homology with murine sequence (in EL4 T cells) at positions 843–1150, as indicated in Table 3. No homology is indicated after position 177 of SEQ ID NO: 5 between the human sequence and the murine sequence. However there is strong homology between the human sequence from pos 228 of SEQ ID NO: 5 with the human thioredoxin sequence.

The oligonucleotide encoding the partial amino acid sequence of human thioredoxin at the N-terminal was the determined and published sequence: Val-Lys-Glu-Ile-Glu-Ser-Lys-Thr-Ala-Phe-Glu-Glu-Ala stated as published unexamined Japanese patent application No. 62 19532 ("Ajinomoto"). Following cloning of the gene for human ADF (thioredoxin) polypeptide and subsequent sequencing the thus determined amino acid sequence accurately contains the human ADF N-terminal amino acid sequence, based upon which the oligonucleotide probe was synthesized. From the sequence it is apparent that the initiating Met for human ADF polypeptide is at position 226 as denoted in SEQ ID NO: 5. The non-coding DNA sequence upstream to the initiating Met does not code for the human ADF polypeptide. The antibodies produced were by using synthetic peptides that were selected from the human ADF sequence encoded by DNA downstream from the initiating Met of the thioredoxin sequence. Subsequently these antibodies were used to detect the expressed protein from the cloned gene.

For the expression of the human ADF polypeptide, the encoding cDNA was specifically selected by cleavage of the cDNA with restriction enzyme BamHI as detailed in Examples 5 and 6 of the Ajinomoto application. The initiating Met for human ADF and the coding region being downstream from the BamHI site, in contrast to the TC-CSF protein for which the initiating Met and coding region is upstream of the BamHI site. Thus the four amino acid sequence overlap between the TC-CSF sequence from position 160 of SEQ ID NO: 5 to the BamHI site that is revealed in FIG. 2 of Ajinomoto was excluded from expression as detailed in Example 5 and 6 of Ajinomoto. Subsequent expression of human ADF using monkey COS cells as host were also cleavage-tested by restriction enzymes whereby the plasmid containing the human ADF construct was specifically selected for expression in the right orientation for the human ADF protein.

Therefore, all of the properties claimed for human ADF polypeptide pertain to cDNA sequence and encoded protein downstream of the initiating Met, corresponding to position 226 of SEQ ID NO: 5, for human ADF and does not include the sequence upstream of the initiating Met. Furthermore it should be noted that the active site of human ADF consists of the sequence Trp-Cys-Gly-Pro-Cys. This sequence is not represented in any form in the TC-CSF portion of the sequence.

In conclusion, the cDNA sequence for TC-CSF with the initiating Met at position 16 of SEQ ID NO: 5, includes the region up to position 225 of SEQ ID NO: 5, that can be cleaved from the thioredoxin sequence at position 174 by BamHI, or BBVI at 230 or TAQ1 at 240, and encodes for a protein that is unique and distinct from the human ADF protein. The human ADF protein being encoded by the initiating Met at position 226 of SEQ ID NO: 5. Therefore, the TC-CSF sequence is novel and encodes for a new and useful protein. Either the gene or the encoded protein can be useful for treatment of disease states in human beings.

The introduction of in vitro clonal assays have provided an extremely useful system with which hematopoiesis can be investigated. The major advantage being the ability to investigate the regulation of proliferation and differentiation of progenitor cells under controlled growth conditions. In this system a progenitor cell as colony forming unit in culture (CFU-c) gives rise to a colony consisting of 50 or more cells under the influence of colony stimulating activity provided by specific growth factor(s). The presence of serum alone in the absence of specific colony stimulating activity does not support consistent colony formation of any significant number. Laboratory controls have revealed that when 100 separate cultures are assayed with adequate progenitor cells, media and serum supplements, with no added specific colony stimulating factor, only 2 to 3 out of 100 cultures may contain 1 colony each. The mitogenic assays utilizing cell lines are relatively non-specific and may well be affected by high background commensurate with the serum concentration in culture. However the CFU-c assay and mitogenic assays are distinctly different. Furthermore, cell lines used in mitogenic assays may be transformed by infection with the v-src oncogene that is a protein kinase, that phosphorylates tyrosine residues and thus converts the cells to lymphokine independent growth. Thus underscoring the utility of the specific CFU-c assay compared with the non-specific mitogenic assay. Hematopoietic progenitor cells, when cultured with TC-CSF in vitro in clonal assays gave rise to colony formation. Control cultures without addition of TC-CSF were utilized in all assays and did not give rise to colony growth, thus indicating the specific activity of the TC-CSF.

This highly specific assay was used to confirm that the colony stimulating activity was encoded by the amino acid residues of the TC-CSF by construction of a synthetic peptide encoding the regions disclosed in SEQ ID NOS: 7, 8, 9, 10, 11, 12, 14, 15 and 16. The data confirmed that specific colony stimulating activity was the property of the amino acid sequence and could not be attributed to excessive serum in the system, concomitant presence of thioredoxin protein, coincidental expression of any vector sequences or cryptic proteins present in the expression system used.

Colony stimulating activity may be well established as correlating with a high degree of specificity to response in patients with blood count increments following treatment with the colony stimulating factor. Assay kits that measure the level of specific colony stimulating factor in patients would then be useful for diagnostic purposes and for monitoring levels during treatment.

Furthermore the TC-CSF may be utilized in vitro for long-term cultures to produce blood cells under safe and controlled conditions that may be utilized for transfusion purposes. This serves to reduce the risk for transfusion transmitted diseases such as HIV and AIDS, hepatitis, CMV etc. Abundant availability of rare cell types would prevent alloimmunization. The gene is useful for gene therapy in patients who that have genetic defects.

Strong homology has been demonstrated in the TC-CSF sequence between murine and human species. Both the murine and human sequence contain GATA motifs that have become recognized as cis-regulatory element in diverse genes, particularly hematopoietic and neuronal regulatory genes. This applies to membrane proteins, growth factor receptor proteins and transcription factors. The effect of cis-regulatory elements on transcription are mediated through the binding of sequence specific nuclear proteins. The nucleotide sequence of TC-CSF and encoded amino acids demonstrate consensus for a signal transduction and transcription regulatory growth factor. In the case of TC-CSF, it has been demonstrated by construction of a synthetic peptide that the partial regions of homology between the murine and human species encode the effector moiety of the protein. Members of the GATA binding protein family are related by virtue of highly conserved protein domains within species. Conservation is strongly maintained among avians, amphibians and mammals.

There is 54% identify over 100 base pairs of human sequence compared with the murine sequence (SEQ ID NOS. 1–16). The pattern is for ten base pairs or three to four amino acids demonstrating homology to occur in strictly sequential order, interrupted by short non-homologous regions. Bioactivity has been demonstrated to be encoded by the regions of homology by synthetic peptides encoding these residues. Transcription factors are known to have some highly conserved sequences within species and cross activity between species is established. Therefore, synthetic peptides may be constructed which contain no more than four sequential amino acid residues of anyone species or a synthetic peptide that may be a chimera and have the activity of a TC-CSF. Reliable methods for predicting antigenic determinants are available in that antibodies bind to 5 to 8 sequential amino acids. The epitopes are at the surface of protein antigens and the more hydrophilic stretches of amino acids are located at the surface of proteins in the native conformation. The epitopes including stereochemical modifications as required would be used in the systematic fabrication of advanced synthetic materials, as reviewed by Mann, *Nature, 365,* 499–505 (1993), that would be useful for long-term maintenance and development of hematopoietic cells in culture and cell processing with applications in transfusion medicine. Thus the present invention includes chimera, substitution, deletions, mutations, peptide mimetics and epitope memetics, and so forth.

In a screen of cytokines for the colony stimulating factor (CSF) that regulates lymphohaematopoiesis, a novel CSF was isolated. The amino acid composition and partial $NH_2$-terminal sequence were determined. The murine complementary DNA was cloned that had features of derivation from an early RNA transcript. The encoded protein occurred in at least two isoforms, consequent to the maturity of the RNA transcript and accordingly encoded site of the initiating methionine. The murine cDNA was used as a probe to clone the human cDNA and nucleotide sequences determined. The synthetic peptide constructed of partial regions of consensus conserved within species demonstrated multilineage CSF activity in culture. The nucleotide sequences with GATA motifs related to cis-regulatory transcription factors and encoded amino acids, supported a model for structural biology facilitated by the soluble protonated agonist receptor with integrated signal transduction region, an effector domain homologous within species and the palindromic domain supported the concept of feedback autoregulation. The carboxyl terminus proline-rich domain shared identity with src homology domains that mediate interactions between proteins and regulate cytoplasmic signalling. The identification of a candidate signal transduction and transcription regulatory factor for lymphohaematopoiesis is of general interest. The provocation of leukeminogenesis and oncogenesis consequent to induction of protein kinase phosphorylation by v-src oncogene expression, that overrides the suppressive mechanism for the usual growth factor signal transduction, enhances the interest in regulation of transcription.

Sequences complementary to the DNA sequences upstream of the cap site are not found in nuclear precursor RNA for most mRNAs, however some mammalian cellular RNA and haematopoietic growth factor RNA have long and short isoforms. The partial amino acid sequences derived from the $NH_2$-terminal of the 55 Kd CSF, isolated from PMA stimulated EL4 conditioned medium were encoded by nucleotide sequences that were upstream of the TATA box of the cloned insert. This supports occurrence of two isoforms of the protein, one encoded by a long mRNA that is under control of promoter sequences and initiating methionine further upstream of the 5' region shown in this sequence (SEQ ID NO. 1 and SEQ ID NO. 2). From that long RNA transcript the entire sequence would be expressed as a 55 Kd protein with 554 amino acids. The other form is the short isoform that is encoded by the sequence with the initiating methionine being 395 bases downstream from the RNA cap site (SEQ ID NO. 1 and SEQ ID NO. 2). The nucleotide sequences downstream from the first GATA motif had consensus for nuclear protein binding sequence, followed by the first zinc finger motif domain of 60 amino acids, CysX3OCysX27His. In that region the first fifteen leucine-rich deduced amino acid residues encoded by a protein kinase C consensus region, had identity that conformed to a signal peptide sequence. The encoded hydrophobic amino acid sequences may serve dual roles, one as a leader or signal peptide to allow secretion of the bioactive protein following cleavage and the other as the transmembrane segment that traverses the cell membrane and may have a role in alignment of the membrane associated isoform.

In the conceptual model the domain consisting of hydrophilic residues contained between proline residues and glycosylation sites, constituted the partial agonist or ligand binding receptor site. Interaction with the protonated residues of that domain caused signal transduction with translocation of the effector domain to nuclear receptors. The bioactive effector domain was concluded to be the regions that share homology with the human sequence, residues 27 through 70 of the human sequence.

The sequence numbers for clone CC2 start with the proline at position 1, that matched position 2 in the amino acid sequence of the isolated 55 KD protein. The nucleotide sequence was determined using the chain termination method, by a combination of double stranded sequencing in the Bluescript™ plasmid using Sequenase version 2.0 T7 DNA polymerase (US Biochemical) and single strand sequencing after subcloning in the M 13 vector. Regions of compression posed technical problems in single strand sequencing of the full clone. Corrections were made for the allosteric effect of C bands, and frame shifts where possible. Some regions apparently encoded Amber and Ochre mutations, while translation of the clone indicated an open reading frame. Consequently amino acid residues that could not be deduced were labelled Xaa. The deduced amino acid sequence is given in the three letter code. Clone CC2 was expressed by inducing the lac promoter with IPTG, in the Bluescript™ vector with fusion protein expression with the B-galactosidase gene product. The partial amino acid sequencing of the isolated 55 Kd protein was compatible with the deduced sequence and indicated the presence of the methionine residue at position 1. The complementary DNA in clone CC2 did not encode this residue and the initiating methionine of clone cc2 was at position 160. The translation product of clone CC2 was approximately 23 Kd. The expressed protein demonstrated bioactivity in vitro, that was encoded by the smaller 23 Kd molecule. The amino acid residues used to design the oligonucleotide probe matched with residues 9 to 15 in the deduced sequence, thus indicating that the sequence encoded two isoforms of protein consequent to the position of the initiating methionine.

In FIG. 3, X denotes any amino acid, the number of residues being indicated by the adjacent numerical. In a conceptual model of clone CC2 promoter sequences P1 and P2 with the TATA box are units for RNA transcription at the +1 mRNA start site with enhancer CAAT regions and the GATA region as cis-regulatory transcriptional activator for haematopoiesis. The transmembrane domain encodes a zinc finger motif and contains leucine rich hydrophobic residues that may function either as a transmembrane domain aiding alignment of the large membrane associated protein isoform, or as a leader or a signal peptide sequence for secretion following cleavage of the smaller bioactive isoform. The carboxyl terminus of the protein encodes a proline-rich domain that identifies with src homology domains that mediate protein interactions and regulate cytoplasmic signalling. This domain connects with hydrophilic residues, between proline residues and glycosylatin sites (O-N-Gly), that probably constitutes part of an agonist or ligand binding receptor (Rc) site, through an apparently palindromic domain to a region that shares identity with reverse complementary sequences to part of the agonist Rc. Interaction with the protonated residues of the agonist Rc induces signal transduction with translocation of the constitutive extracytoplasmic effector domain to nuclear receptors and consequent transcription of haematopoiesis. The palindromic domain supports a model for the concept of autoregulation that may occur between the agonist Rc and the region encoding agonist rc reverse complementary sequences, that may act in either orientation and the palindromic domain that may act in either direction. Thus the present invention includes within its scope anti-sense oligonucleotides and so forth that have diagnostic and therapeutic applications.

Although the present invention is described herein in terms of preferred embodiments, it is expected that modifications and variations will occur to those skilled in the art upon consideration of the present invention. It is intended that the present invention encompass all such modifications and variations which come within the scope of the claims.

What is claimed is:

1. A purified and isolated protein having a peptide sequence consisting of amino acids 6 through 75 as shown in SEQ ID NO: 6.

2. A pharmaceutical composition consisting essentially of the protein according to claim 1 in a pharmaceutically-acceptable carrier.

3. The protein according to claim 1 further consisting of a label.

4. The protein according to claim 1 attached to a support.

* * * * *